US007811566B2

(12) United States Patent
Arakawa et al.

(10) Patent No.: US 7,811,566 B2
(45) Date of Patent: Oct. 12, 2010

(54) ANTIBODY-INDUCED APOPTOSIS

(75) Inventors: Tsutomu Arakawa, Thousand Oaks, CA (US); Yoshiko Kita, Thousand Oaks, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 11/981,562

(22) Filed: Oct. 30, 2007

(65) Prior Publication Data
US 2009/0142359 A1 Jun. 4, 2009

Related U.S. Application Data

(60) Division of application No. 09/994,068, filed on Nov. 27, 2001, now Pat. No. 7,354,583, which is a continuation of application No. 09/046,785, filed on Mar. 23, 1998, now Pat. No. 6,458,356, which is a continuation of application No. 08/568,072, filed on Dec. 5, 1995, now Pat. No. 5,783,186.

(51) Int. Cl.
*A61K 39/395* (2006.01)

(52) U.S. Cl. ............. 424/143.1; 424/130.1; 424/138.1; 424/141.1; 424/142.1

(58) Field of Classification Search ........................ None
See application file for complete search history.

(56) References Cited

U.S. PATENT DOCUMENTS

| | | | |
|---|---|---|---|
| 4,676,980 A | 6/1987 | Segal et al. | |
| 4,954,617 A | 9/1990 | Fanger et al. | |
| 5,001,225 A | 3/1991 | Taylor | |
| 5,489,525 A | 2/1996 | Pastan | |
| 5,677,171 A * | 10/1997 | Hudziak et al. | 435/7.23 |
| 5,720,937 A | 2/1998 | Hudziak et al. | |
| 5,725,856 A | 3/1998 | Hudziak et al. | |
| 5,770,195 A | 6/1998 | Hudziak et al. | |
| 5,772,997 A | 6/1998 | Hudziak et al. | |
| 5,783,186 A | 7/1998 | Arakawa et al. | |
| 5,869,268 A | 2/1999 | Kudo et al. | |
| 5,910,486 A | 6/1999 | Curiel et al. | |
| 6,165,464 A | 12/2000 | Hudziak et al. | |
| 6,387,371 B1 | 5/2002 | Hudziak et al. | |
| 6,399,063 B1 | 6/2002 | Hudziak et al. | |
| 6,458,356 B1 * | 10/2002 | Arakawa et al. | 424/155.1 |
| 7,354,583 B2 * | 4/2008 | Arakawa et al. | 424/143.1 |

FOREIGN PATENT DOCUMENTS

| | | |
|---|---|---|
| JP | 5317084 | 12/1993 |
| WO | WO 94/00136 | 1/1994 |
| WO | WO 96/07321 | 3/1996 |
| WO | WO 98/17797 A1 | 4/1998 |

OTHER PUBLICATIONS

Kita et al, Biochemical and Biophysical Research Communications, 1996, 226:59-69, IDS.*

In re Alonso, Oct. 2008, US Court of Appeals for the Federal Circuit (p. 1-11 + cover).*
Phillips et al., "Targeting HER2-Positive Breast Cancer with Transtuzumab-DM1, an Antibody-Cytotoxic Drug Conjugate," Cancer Res., 68(22): 9280-9290 (2008).
Yarden et al., "Growth Factor Receptor Tyrosine Kinases," Ann. Rev. Biochem., 57: 443-478 (1988).
Summons to attend oral proceedings pursuant to Rule 115(1) EPC dated Feb. 26, 2008, for European Patent Application No. 96943576.7 (4 pages).
Response to the Summons mailed Aug. 1, 2008, for European Patent Application No. 96943576.7 (9 pages).
Interlocutory decision in Opposition proceedings (Art. 101(3)(a) and 106(2) EPC) dated Dec. 11, 2008, for European Patent Application No. 96943576.7 (47 pages).
Provision of the minutes in accordance with Rule 124(4) EPC dated Dec. 11, 2008, for European Patent Application No. 96943576.7 (15 pages).
Opponent-Appellant's Grounds of appeal filed Apr. 21, 2009, for European Patent Application No. 96943576.7 (17 pages).
In Response to the Opponent-Appellant's Grounds of Appeal filed Sep. 25, 2009, for European Patent Application No. 96943576.7 (14 pages).
Official Communication dated Jan. 9, 2009, for European Patent Application No. 03018949.2 (6 pages).
Response to Official Communication and request for further processing filed Nov. 5, 2009, for European Patent Application No. 03018949.2 (3 pages).
Arakawa et al., *Arch. Biochem. Biophs.*, 308: 267-273 (1994).
Bargmann et al., *The Oncogene Handbook*, pp. 107-119 (1988).
Berchuck et al., *Cancer Res.*, 50: 4087-4091 (1990).
Campos-Gonzalez et al., *Growth Factors*, 4 (4): 305-316 (1991).
Curiel, *Gene Therapy*, 2: 20 (1995).
Coussens et al., *Science* 230: 1132-1139 (1985).
Deshane et al., *Gynecol. Oncol.* 59: 8-14 (1995).
Deshane et al., *Journal of Investigative Medicine* 32: 328A (1995).
Drevin et al., *Oncogene* 2: 387-394 (1988).
Falls et al., *Cell* 72: 801-815 (1993).
Fendly et al., *Cancer Res.*, 50: 1550-1558 (1990).
Fukushige et al., *Mol. Cell Biol.*, 6: 955-958 (1986).
Grim et al., *Cancer Gene Therapy*, 1: 333-334 (1994).
Harwerth et al., *Br. J. Cancer*, 68: 1140-1145 (1993).
Harlow and Lane, *Antibodies: A Laboratory Manual*, Cold Spring Harbor Laboratory (1988).
Holmes et al., *Science*, 256: 1205-1210 (1992).
Hudziak et al., *Mol. Cell Biol.*, 9: 1165-1172 (1989).
Kallioniemi et al., *Int. J. Cancer*, 49: 650-655 (1991).
Kelley et al., *Biochemistry*, 31: 5434-5441 (1992).
Kerr et al., *Br. J. Cancer*, 26: 239-257 (1972).
King et al., *Science*, 229: 974-976 (1985).
Kita et al., *Biochemical and Biophysical Research Communications*, 226: 59-69 (1996).

(Continued)

*Primary Examiner*—Laura B Goddard
(74) *Attorney, Agent, or Firm*—Finnegan, Henderson, Farabow, Garrett & Dunner, L.L.P.

(57) ABSTRACT

Anti-Her2 antibodies which induce apoptosis in Her2 expressing cells are disclosed. The antibodies are used to "tag" Her2 overexpressing tumors for elimination by the host immune system. Also disclosed are hybridoma cell lines producing the antibodies, methods for treating cancer using the antibodies, and pharmaceutical compositions.

12 Claims, 11 Drawing Sheets

OTHER PUBLICATIONS

Korman et al., *Proc. Natl. Acad. Sci. USA*, 84: 2150-2154 (1987).
Kraus et al., *Proc. Natl. Acad. Sci. USA*, 86: 9193-9197 (1989).
Lin et al., *Gene*, 44: 201-209 (1986).
Maniatis et al., *Molecular Cloning: A Laboratory Manual*, Cold Spring Harbor, New York: Cold Spring Harbor Laboratory (1982).
Marchionni et al., *Nature*, 362: 312-318 (1993).
Mendelsohn, *Cancer Cells*, 7: 359-362 (1989).
Muss et al., *N. Engl. J. Med*, 330: 1260-1266 (1994).
Philo et al., *J. Biol. Chem.*, 269: 27840-27846 (1994).
Plowman et al., *Proc. Natl. Acad. Sci. USA*, 90: 1746-1750 (1993).
Press et al., in *Effects of Therapy on Biology and Kinetics of the Residual Tumor*, Part A: Preclinical Aspects pp. 209-221 (1990).
*Remington's Pharmaceutical Sciences*, 18$^{th}$ ed. A.R. Gennaro, ed. Mack, Easton, PA (1990).
Rilke et al., *Int. J. Cancer*, 49: 44-49 (1991).
Ro et al., *Cancer Res.*, 49: 6941-6944 (1989).
Savill et al., *Nature*, 343: 170-173 (1990).
Schechter et al., *Nature*, 312: 515-516 (1984).
Seaver, *Gen Eng. News.*, 14(4): 10 and 21 (1994).
Semba et al., *Proc. Natl. Acad. Sci. USA*, 82: 6497-6501 (1985).
Slamon et al., *Science*, 235: 177-182 (1987).
Slamon et al., *Science*, 244: 707-712 (1989).
Srinivas et al., *Cancer Immunol. Immunother*, 36: 397-402 (1993).
Stancovski et al., *Proc. Natl. Acad. Sci. USA*, 88: 8691-8695 (1991).
Tagliabue et al., *Int. J. Cancer*, 47: 933-937 (1991).
Takagi, *J. Chromatogr.*, 506: 409-446 (1990).
Vitetta and Uhr, *Cancer Res.*, 54: 5301-5309 (1994).
Wright et al., *Cancer Res.*, 49: 2087-2090 (1989).
Wu et al., *J. Clin. Invest.*, 95: 1897-1905 (1995).
Wyllie, A., *Int. Rev. Cytol.*, 68: 251-306 (1980).
Wyllie et al., *Nature*, 284: 555-556 (1980).
Xu et al., *Int. J. Cancer.*, 53: 401-408 (1993).
Yarden, *Proc. Natl. Acad. Sci. USA*, 87: 2569-2573 (1990).
Walker et al., *Brit. J. Cancer*, 60: 426-429 (1989).
Wen et al., *Cell*, 69: 559-572 (1992).
Hudziak, Robert M. et al., "Amplified expression of the HER2/ERBB2 oncogene induces resistance to tumor necrosis factor α in NIH 3T3 cells," *Proc. Natl. Acad. Sci. USA*, 85:5102-5106 (1988).
European Search Report, for counterpart European Application No. 03 01 8949, dated Nov. 10, 2003.
Deshane et al., "Intracellular single-chain antibody directed against erbB2 down-regulates cell surface erbB2 and exhibits a selective anti-proliferative effect in erbB2 overexpressing cancer cells lines," Gene Therapy, 1: 332-337 (1994).
George et al., "Redirection of T cell-mediated cytotoxicity by a recombinant single-chain fv molecule," Journal of Immunology, 152: 1802-1811 (1994).
Gruber et al., "Efficient tumor cell lysis mediated by a bispecific single chain antibody expressed in *Escherichia coli*," Journal of Immunology, 152: 5368-5374 (1994).
Harris et al., "The induction of apoptosis in human mammary luminal epithelial cells by expression of activated c-*neu* and its abrogation by glucocorticoids," British Journal of Cancer, 72: 386-392 (1995).
Kyakumoto et al., "Co-expression of epidermal growth factor-receptor and c-*erb* B-2 proto-oncogene product in human salivary-gland adenocarcinoma cell line HSG and the implications for HSG cell autocrine growth," Archives of Oral Biology, 39(7): 569-580 (1994).
Lippman et al., "The role of the erbB2 receptor and its ligands in human breast cancer," Journal of Immunotherapy, 14(4): 369 (1993).
Freshney, Culture of Animal Cells, A Manual of Basic Technique, Alan R. Liss, Inc., 1983, New York, p. 4.
Dermer, Bio/Technology, 1994, 12: 320.
Drexler et al., Leukemia and Lymphoma, 1993, 9: 1-25.
Gura, Science, 1997, 278: 1041-1042.
Jain, Sci. Am., 1994, 271: 58-65.
Curti, Crit. Rev. in Oncology/Hematology, 1993, 14: 29-39.
Stancovski et al., PNAS, USA, 1991, 88: 8691-8695.
Lewis et al., Cancer Immunology Immunotherapy, 1993, 37: 255-263.
Strobel et al., Gynecologic Oncology, 1999, 73: 362-367.
Voskoglou-Nomikos et al., Clinical Cancer Research, 2003, 9: 4227-4239.
Cell Lines in the In Vitro Screen, p. 1-3, printed Apr. 10, 2006.
MDA-MB-435: Breast or Melanoma Origin?, printed Apr. 10, 2006.
Shepard et al., J of Clinical Immunology, 1991, 11: 117-127.
Le et al., Clinical Cancer Research, 2000, 6: 260-270.
Mohsin et al., J Clin Oncology, 2005, 23: 2460-2468.
Bussolati et al., British J of Cancer, 2005, 92: 1261-1267.
Reichmann et al., Nature, 1988, 332: 323-327.
Office Action mailed Apr. 30, 1997, for U.S. Appl. No. 08/568,072, filed Dec. 5, 1995 (19 pages).
Response filed Sep. 2, 1997, for U.S. Appl. No. 08/568,072, filed Dec. 5, 1995 (10 pages).
Notice of Allowance and Issue Fee Due mailed Dec. 9, 1997, for U.S. Appl. No. 08/568,072, filed Dec. 5, 1995 (7 pages).
Office Action mailed Aug. 17, 1999, for U.S. Appl. No. 09/046,785, filed Mar. 23, 1998 (10 pages).
Response to Office Action filed Feb. 16, 2000, for U.S. Appl. No. 09/046,785, filed Mar. 23, 1998 (10 pages).
Final Office Action mailed May 10, 2000, for U.S. Appl. No. 09/046,785, filed Mar. 23, 1998 (9 pages).
Response under 37 CFR §1.116, filed Oct. 10, 2000, for U.S. Appl. No. 09/046,785, filed Mar. 23, 1998 (6 pages).
Advisory Action mailed Jan. 3, 2001, for U.S. Appl. No. 09/046,785, filed Mar. 23, 1998 (8 pages).
Amendment filed Jun. 11, 2001, for U.S. Appl. No. 09/046,785, filed Mar. 23, 1998 (9 pages).
Notice of Allowance and Issue Fee Due mailed Aug. 27, 2001, for U.S. Appl. No. 09/046,785, filed Mar. 23, 1998 (5 pages).
Office Action mailed Sep. 22, 2005, for U.S. Appl. No. 09/994,068, filed Nov. 27, 2001 (27 pages).
Amendment and Response filed Feb. 2, 2006, for U.S. Appl. No. 09/994,068, filed Nov. 27, 2001 (25 pages).
Final Office Action mailed Apr. 19, 2006, for U.S. Appl. No. 09/994,068, filed Nov. 27, 2001 (19 pages).
Response After Final filed Aug. 21, 2006, for U.S. Appl. No. 09/994,068, filed Nov. 27, 2001 (23 pages).
Advisory Action mailed Oct. 13, 2006, for U.S. Appl. No. 09/994,068, filed Nov. 27, 2001 (3 pages).
Office Action mailed Jan. 25, 2007, for U.S. Appl. No. 09/994,068, filed Nov. 27, 2001 (26 pages).
Amendment and Response filed Jul. 25, 2007, for U.S. Appl. No. 09/994,068, filed Nov. 27, 2001 (26 pages).
Facsimile of proposed Examiner's Amendment sent Sep. 26, 2007, for U.S. Appl. No. 09/994,068, filed Nov. 27, 2001 (2 pages).
Transmittal Letter with Interview Summary and Terminal Disclaimer filed Sep. 26, 2007, for U.S. Appl. No. 09/994,068, filed Nov. 27, 2001 (6 pages).
International Search Report mailed Mar. 26, 1997, for International Patent Application No. PCT/US96/19289, filed Dec. 4, 1996. (9 pages).
Written Opinion mailed Jan. 21, 1998, for International Patent Application No. PCT/US96/19289, filed Dec. 4, 1996. (4 pages).
International Preliminary Examination Report mailed Jun. 4, 1998, for International Patent Application No. PCT/US96/19289, filed Dec. 4, 1996. (5 pages).
Examiner's First Report mailed Oct. 20, 1998, for Australian Patent Application No. 12784/97 (AU national phase filing of International Application No. PCT/US96/19289, filed Dec. 4, 1996 (2 pages).
Response to Examiner's First Report filed Apr. 20, 2000, for Australian Patent Application No. 12784/97 (AU national phase filing of International Application No. PCT/US96/19289, filed Dec. 4, 1996 (10 pages).
Examiner's Report No. 2 mailed May 1, 2000, for Australian Patent Application No. 12784/97 (AU national phase filing of International Application No. PCT/US96/19289, filed Dec. 4, 1996 (1 page).
Memorandum in Response to the Office Action of 21 May 2001, filed Feb. 21, 2002, for Israeli Patent App. No. 124,689 (IL national phase filing of International Application No. PCT/US96/19289, filed Dec. 4, 1996) (6 pages).
Examiner's Report mailed Jul. 24, 1998, for New Zealand Patent App. No. 324982 (NZ national phase filing of International Application No. PCT/US96/19289, filed Dec. 4, 1996) (6 pages).

Response filed Jan. 21, 2000, for New Zealand Patent App. No. 324982 (NZ national phase filing of International Application No. PCT/US96/19289, filed Dec. 4, 1996) (9 pages).
Examination Report mailed Feb. 1, 2000, for New Zealand Patent App. No. 324982 (NZ national phase filing of International Application No. PCT/US96/19289, filed Dec. 4, 1996) (1 page).
Official Action mailed Dec. 2, 2002, for Canadian Patent Application No. 2,236,913 (CA national phase filing of International Application No. PCT/US96/19289, filed Dec. 4, 1996) (3 pages).
Response to Official Action filed Jun. 2, 2003, for Canadian Patent Application No. 2,236,913 (CA national phase filing of International Application No. PCT/US96/19289, filed Dec. 4, 1996) (18 pages).
Official Action mailed Oct. 7, 2003, for Canadian Patent Application No. 2,236,913 (CA national phase filing of International Application No. PCT/US96/19289, filed Dec. 4, 1996) (3 pages).
Response to Official Action mailed Apr. 6, 2004, for Canadian Patent Application No. 2,236,913 (CA national phase filing of International Application No. PCT/US96/19289, filed Dec. 4, 1996) (6 pages).
Communication Pursuant to Article 96(2) EPC mailed Apr. 17, 2001, for European Patent Application No. 96943576 (EP national phase filing of International Application No. PCT/US96/19289, filed Dec. 4, 1996) (7 pages).
Response to the Official Communication filed Nov. 27, 2001, for European Patent Application No. 96943576 (EP national phase filing of International Application No. PCT/US96/19289, filed Dec. 4, 1996) (7 pages).
Communication Pursuant to Article 96(2) EPC mailed Feb. 25, 2002, for European Patent Application No. 96943576 (EP national phase filing of International Application No. PCT/US96/19289, filed Dec. 4, 1996) (4 pages).
Response to the Official Communication filed Jul. 4, 2002, for European Patent Application No. 96943576 (EP national phase filing of International Application No. PCT/US96/19289, filed Dec. 4, 1996) (12 pages).
Communication under Rule 51(4) EPC mailed Apr. 14, 2003, for European Patent Application No. 96943576 (EP national phase filing of International Application No. PCT/US96/19289, filed Dec. 4, 1996) (6 pages).
Communication of a Notice of Opposition mailed Jul. 20, 2004, for European Patent Application No. 96943576 (EP national phase filing of International Application No. PCT/US96/19289, filed Dec. 4, 1996). (20 pages), Certified Translation Included.
Communication of Notice of Opposition (R. 57(1) EPC) mailed Aug. 13, 2004, for European Patent Application No. 96943576 (EP national phase filing of International Application No. PCT/US96/19289, filed Dec. 4, 1996) (1 page).
Comments on Opponent's Submission filed Mar. 18, 2005, for European Patent Application No. 96943576 (EP national phase filing of International Application No. PCT/US96/19289, filed Dec. 4, 1996) (12 pages).
Communication Pursuant to Article 101(2) and Rule 58(1) to (3) EPC mailed Jul. 21, 2006, for European Patent Application No. 96943576 (EP national phase filing of International Application No. PCT/US96/19289, filed Dec. 4, 1996) (8 pages).
Response to Preliminary Opinion of the Opposition Division filed Jan. 31, 2007, for European Patent Application No. 96943576 (EP national phase filing of International Application No. PCT/US96/19289, filed Dec. 4, 1996) (6 pages).
Communication Pursuant to Article 96(2) EPC mailed Dec. 20, 2005, for European Patent Application No. 03018949 (Divisional of European Patent Application No. 96943576, which is an EP national phase filing of International Application No. PCT/US96/19289, filed Dec. 4, 1996) (8 pages).
Response to Official Communication filed Jun. 30, 2006, for European Patent Application No. 03018949 (Divisional of European Patent Application No. 96943576, which is an EP national phase filing of International Application No. PCT/US96/19289, filed Dec. 4, 1996) (11 pages).
Communication Pursuant to Article 96(2) EPC mailed Aug. 1, 2006, for European Patent Application No. 03018949 (Divisional of European Patent Application No. 96943576, which is an EP national phase filing of International Application No. PCT/US96/19289, filed Dec. 4, 1996) (6 pages).
Response to Official Communication filed Feb. 12, 2007, for European Patent Application No. 03018949 (Divisional of European Patent Application No. 96943576, which is an EP national phase filing of International Application No. PCT/US96/19289, filed Dec. 4, 1996) (7 pages).

* cited by examiner

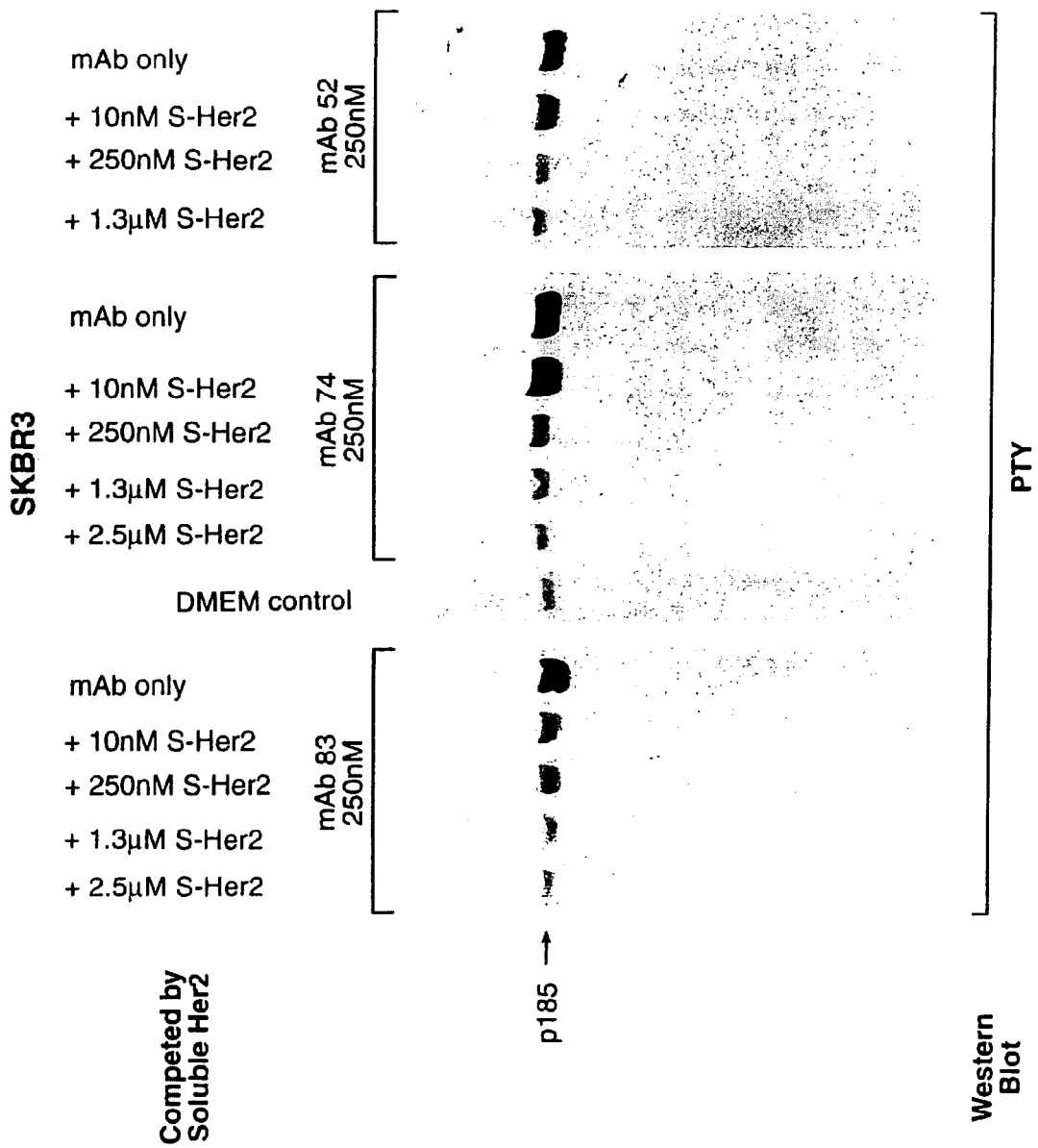

ANTIBODY-INDUCED APOPTOSIS

This application is a divisional of U.S. patent application Ser. No. 09/994,068, filed Nov. 27, 2001, now U.S. Pat. No. 7,354,583, which is a continuation of U.S. patent application Ser. No. 09/046,785, filed Mar. 23, 1998, now U.S. Pat. No. 6,458,356, which is a continuation of U.S. patent application Ser. No. 08/568,072, filed Dec. 5, 1995, now U.S. Pat. No. 5,783,186, all of which are incorporated herein by reference in their entirety.

FIELD OF THE INVENTION

The present invention relates to anti-Her2 antibodies and more particularly to anti-Her2 antibodies which induce apoptosis in Her2 expressing cells.

BACKGROUND OF THE INVENTION

The Her2 oncogene encodes a membrane-associated glycoprotein referred to as $p185^{HER-2}$ having tyrosine kinase activity. Her2 is a member of the epidermal growth factor (EGF) receptor subfamily, which includes EGF receptor and Her3 and Her4 receptors (Kraus et al. Proc. Natl. Acad. Sci. USA 86, 9193-9197 (1989); Plowman et al. Proc. Natl. Acad. Sci. USA 90, 1746-1750 (1993)). The Her2 sequence was reported by Semba et al. (Proc. Natl. Acad. Sci. USA 82, 6497-6501 (1985)); Coussens et al. (Science 230, 1132-1139 (1985)) and King et al. (Science 229, 974-976 (1985)). A related rat gene was reported by Schecter et al (Nature 312, 515-516 (1984)).

Increased expression of the Her2 oncogene in tumor cells and cell lines has been reported by several groups (Coussens et al., supra; King et al., supra). The increased expression of Her2 results from gene amplification or increased expression of the single copy gene. These observations suggested that Her2 may be overexpressed in human cancer tissue. Slamon and colleagues (Slamon et al. Science 235, 177-182 (1987); Slamon et al. Science 244, 707-712 (1989)) examined Her2 expression levels in tumors taken from a large sample of breast and ovarian cancer patients. It was found that nearly 30% of those patients had amplification and over-expression of the Her2 gene which was associated with a poor clinical outcome (increased relapse and low survival rate) particularly in node-positive breast cancer patients. The correlations reported by Slamon have been confirmed in a number of studies (see, for example, Ro et al. Cancer Res. 49, 6941-6944 (1989); Walker et al. Brit. J. Cancer 60, 426-429 (1989); Wright et al. Cancer Res. 49, 2087-2090 (1989); Berchuck et al. Cancer Res 50, 4087-4091 (1990); Kallioniemi et al. Int. J. Cancer 49, 650-655 (1991); Rilke et al. Int. J. Cancer 49, 44-49 (1991)).

The presence of certain factors, such as Her2 overexpression, that are indicative of a poor prognosis may suggest that adjuvant therapy after surgical removal of the tumor is appropriate. Adjuvant therapy can include high dose chemotherapy and autologous bone marrow transplantation. It has recently been reported (Muss et al. N. Engl. J. Med. 330, 1260-1266 (1994)) that breast cancer patients having tumors displaying Her2 overexpression enjoyed significant benefits from adjuvant therapy.

By analogy with other receptor protein tyrosine kinases, it is assumed that a ligand for Her2 stimulates receptor phosphorylation. A number of polypeptide factors have been reported to increase tyrosine phosphorylation of Her2 and were presumed to be a ligand (Wen et al. Cell 64, 559-572 (1992); Holmes et al. Science 256, 1205-1210; Marchionni et al. Nature 362, 312-318 (1993); Falls et al. Cell 72, 801-815 (1993)). However, there is no evidence that any of these factors are true ligands which bind directly to Her2 and stimulate receptor phosphorylation. One approach to circumvent the absence of ligand is to generate a ligand-like monoclonal antibody (mAb). Several groups have generated anti-Her2 mAbs using either a cell-surface Her2 receptor or a purified extracellular domain of Her2 receptor (Yarden, Proc. Natl. Acad. Sci. USA 87, 2569-2573 (1990); Hanwerth et al. Br. J. Cancer 68, 1140-1145 (1993); Srinivas et al. Cancer Immunol. Immunother. 36, 397-402 (1993); Stancovaski et al. Proc. Natl. Acad. Sci. USA 88, 8691-8695 (1991)). These mAbs stimulated tyrosine phosphorylation of Her2 from overexpressing cells, but were not fully characterized in terms of binding to and phosphorylation of each of Her2, Her3 or Her4 or in terms of the kinase activation in Her2 transfected cells.

Growth inhibitory effects of anti-Her2 mAbs on breast cancer cells have been reported previously (Tagliabue et al. Int. J. Cancer 47, 933-937 (1991); Hudziak et al. Mol. Cell. Biol. 9, 1165-1172 (1989); Drevin et al. Oncogene 2, 387-394 (1988); Fendly et al. Cancer Res. 50, 1550-1558 (1990); Hanwerth et al., supra; see also review by Vitetta and Uhr, Cancer Res. 54, 5301-5309 (1994)), but these effects were interpreted to be cytostatic since removal of antibody allowed resumption of cell growth. Xu et al. (Int. J. Cancer 53, 401-408 (1993)) reported anti-Her2 antibodies which were cytotoxic for anchorage-independent tumor cell growth.

An anti-EGF receptor mAb was reported to induce apoptosis on the human colorectal carcinoma cell line, DiFi, which overexpresses EGF receptor, and to induce morphological changes at concentrations of 5 to 20 nM. These effects were interpreted in terms of both blockage of EGF binding to the cognate receptor by the competing mAb and lack of the mAb mitogenic activity (Wu et al. J. Clin. Invest. 95, 1897-1905 (1995)).

Apoptosis, or programmed cell death, is a form of cell death characterized by cell shrinkage and DNA fragmentation. Collapse of the cell nucleus is apparent as chromation is fragmented into single or multiple mononucleosomal units, a process mediated by an endogenous endonuclease. Apoptosis is distinct from necrotic cell death which results in cell swelling and release of intracellular components (Kerr et al. Br. J. Cancer 26, 239-257 (1972); Wyllie et al. Int. Rev. Cytol. 68, 251-306 (1980); Wyllie Nature 284, 555-556 (1980)). Apoptotic cells, without releasing such components, are phagocytosed and hence degraded (Savill et al. Nature 343, 170-173 (1990)). Therefore, apoptosis results in an efficient process for elimination of nonviable cells by the host's own defense mechanisms.

It is an object of the invention to generate antibodies to Her2 which induce apoptosis in Her2 expressing cells and thereby "tag" such cells for removal from the host. The antibodies are useful for inducing apoptosis in tumors. This represents a substantial improvement over currently available antibody therapy for cancer which typically involves killing tumor cells by antibody in conjunction with a cytotoxic agent. Cytotoxic agents generally produce undesirable side effects which, if severe, can lead to a reduction or interruption of treatment. The present approach allows for killing of tumor cells by the host immune system, thereby avoiding the effects of cytotoxic agents and tumor cell necrosis induced by such agents.

SUMMARY OF THE INVENTION

Antibodies which induce apoptosis in cells expressing Her2 are provided by the invention. It has been found that an antibody which stimulates phosphorylation of Her2 receptors in cell lines also has the unexpected effect of inducing changes in Her2 expressing cells characteristic of apoptosis. These changes include DNA fragmentation and loss of viability and are observed in the treated cell population within 24 hours. Such an antibody is useful for tagging Her2 overexpressing cells for elimination by host defense mechanisms.

The antibodies of the invention may recognize an epitope on Her2 which is recognized by the mAb74 antibody. The epitope was distinct from epitopes recognized by other antibodies which also bound to Her2 but did not induce apoptosis, suggesting that the region of Her2 which interacts with antibody is important in eliciting an apoptotic response. Antibodies that induce apoptosis may exist as full-length antibodies having intact variable and constant regions or fragments thereof which retain Her2 binding and apoptosis. The antibodies may be produced by hybridoma cell lines or by recombinant DNA methods.

Methods for treating cancers characterized by Her2 overexpression are encompassed by the invention. A number of cancers, including breast, ovarian, prostate and colorectal cancers, are predicted to be more invasive and thus more lethal when they exhibit overexpression of Her2. The correlation between Her2 expression and poor prognosis (increased relapse and higher mortality) in certain cancers has made Her2 an attractive target for cancer therapeutics. The present invention provides a method for targeting the elimination of cancer cells overexpressing Her2 by inducing apoptosis in said cells.

Pharmaceutical compositions comprising the antibodies of the invention in a pharmaceutically acceptable adjuvant are also provided.

DESCRIPTION OF THE FIGURES

FIG. 3. Inhibition by soluble Her2 receptor of receptor tyrosine phosphorylation induced by mAb. Phosphorylation assay is similar to that described in FIG. 2. Cells were incubated with 250 nM mAb with different concentrations of sHer2.

DETAILED DESCRIPTION OF THE INVENTION

Figures 1A, 1B:
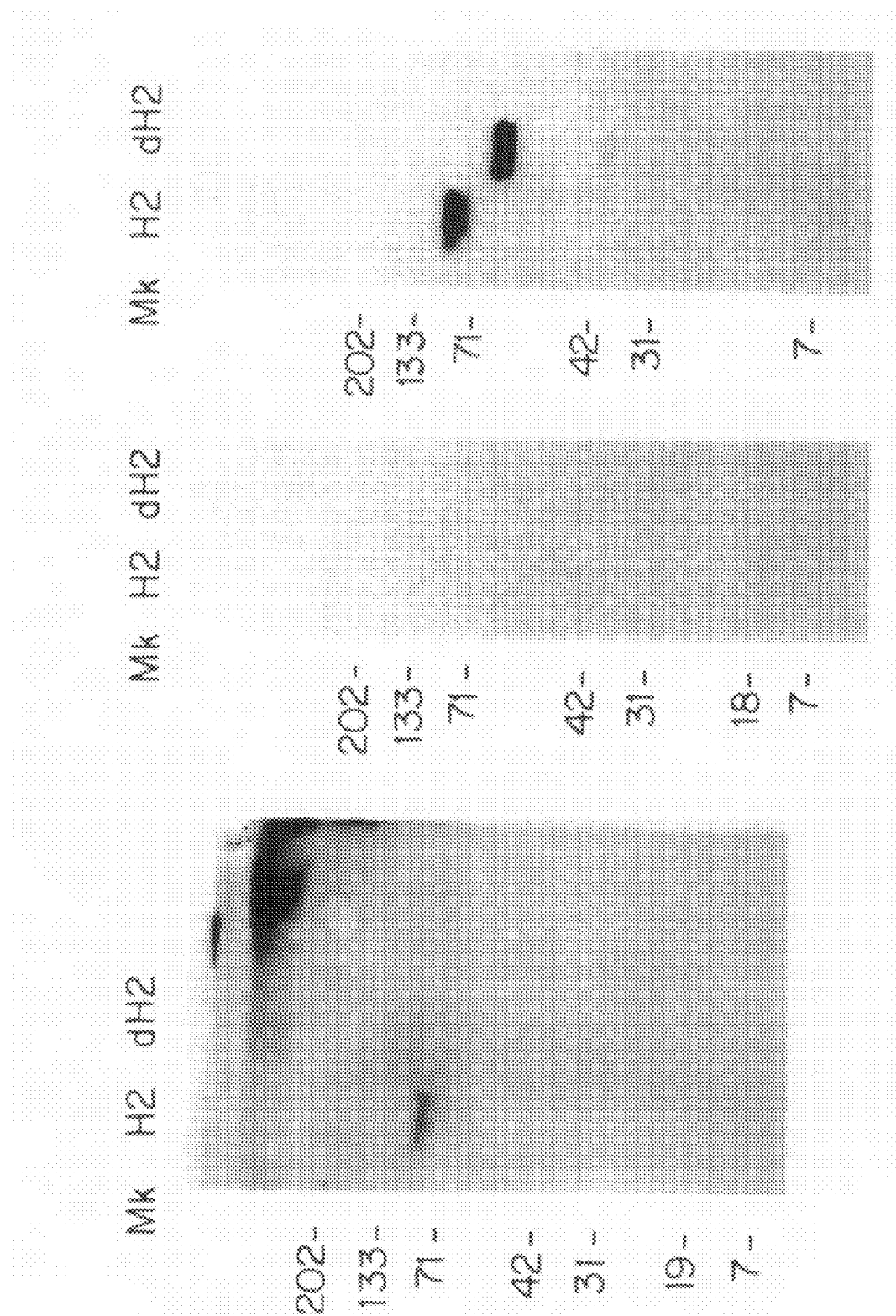
FIG. 1. Binding of mAb74 to glycosylated and deglycosylated sHer2 by Western blot analysis. (a) Extent of Her2 deglycosylation by CHO staining after nonreducing SDS-PAGE; (b) Binding of mAb74 to glycosylated and deglycosylated Her2 as analyzed by Western blotting after nonreducing SDS-PAGE.

Monoclonal antibodies (mAbs) which bind to Her2 have been generated by immunizing mice with purified soluble Her2. Soluble Her2 was expressed and purified as described in Example 1. Mabs which bound to soluble Her2 in enzyme-linked immunosorbent assays (EIA) were subjected to dilution cloning and rescreening by EIA and BIAcore for binding to Her2 (Example 2). Ten clones were selected for further analysis. Purified antibodies from these clones were found to preferentially bind soluble Her2 and showed little or no binding to soluble Her3 and Her4. The biological effects of selected antibodies were studied for receptor dimerization, receptor phosphorylation and changes in cell physiology. All the antibodies tested formed 2:1 (receptor:antibody) complexes with Her2 (Example 4). Three different antibodies stimulated phosphorylation of Her2 and Her3 receptors on SKBR3 cells and Her2, Her3 and Her4 receptors on MDAMB453 cells. Phosphorylation of all receptors was inhibited by soluble Her2, suggesting that the ligand-like effects of the mabs are mediated directly through Her2.

One antibody, mAb74, induced dramatic changes in the physiology of cells expressing Her2 (Examples 5 and 6). Treatment of MCF7 cells transfected with a full-length Her2 gene or treatment of MDAMB453 cells which naturally express Her2 with mAb74 resulted in a marked change in cell morphology and extensive cell death. One other antibody, mAb83, showed a moderate effect on cell morphology. In those cells which were nonviable, apoptosis had been induced as evidenced by extensive DNA fragmentation. However, a subpopulation of cells escaped the activity of mAb74 and were not apoptotic.

The invention provides for an antibody or fragment thereof which induces apoptosis in Her2 expressing cells. As used herein, the term "apoptosis" denotes programmed cell death characterized by nuclear collapse and DNA degradation. Cells undergoing apoptosis in response to the antibodies of the invention will have at least Her2 on the cell surface and optionally Her3 and Her4. It is preferred that the cells or tissues being targeted exhibit levels of expression of Her2 that are greater than a normal basal level. Her2 overexpression may be at least 10% higher than a normal basal level, or more preferably 20% higher, or more preferably 30% higher. As used herein, the term "Her2 overexpression" refers to any level of Her2 expression which is greater than the normal basal level. As indicated in the Background section, various cancers are characterized by Her2 overexpression. A basal level of Her2 expression is typically that measured in non-cancerous tissues and cells which express Her2.

Antibodies of the invention bind to an epitope of Her2 such that binding results in Her2 dimerization, Her2 phoshorylation and cell apoptosis. As used herein, the term "epitope" refers to a region of Her2 bound by an antibody which is protected from binding by a second antibody. In a preferred embodiment, the epitope is defined by the binding of mAb74 to Her2. This epitope is distinct from epitopes recognized by other anti-Her2 antibodies (see Table 1). It is noteworthy that other anti-Her2 antibodies induce Her2 dimerization and phosphorylation, but not apoptosis, and recognize epitopes on Her2 that are distinct from that recognized by mAb74.

Antibodies of the invention may be polyclonal or monoclonal or fragments thereof. Murine polyclonal and monoclonal antibodies are produced by standard immunological techniques. Antibody fragments encompass those antibodies which interact specifically with Her2 and induce apoptosis in cells and tissues expressing Her2. As indicated below in the examples, there is a correlation between apoptotic activity of mAb74 and Her2 receptor phosphorylation and dimerization. Therefore, it is preferred that the antibody fragments of the invention-retain their bivalent structure which is likely to promote receptor dimerization and activation. Also encompassed are antibodies made by recombinant means such as chimeric antibodies (variable region and constant region derived from different species) and CDR-grafted antibodies (complementary determining region derived from a different species) as described in U.S. Pat. Nos. 4,816,567 and 5,225,539. Preferably, the antibodies are at least partly of human origin. These include humanized antibodies, typically produced by recombinant methods, wherein the human sequences comprise part or all of the antibody. Also included are fully human antibodies produced in genetically-altered mice (see PCT Application No. 93/12227).

Antibodies of the invention may also have a detectable label attached thereto. The label may be a fluorescent, enzymatic, affinity or isotopic label. Examples include fluorescein isothiocyanate (FITC) for detection by fluorescence, horseradish peroxidase which allows detection by cleavage of a chromogenic substrate, radioisotopes such as $I^{125}$ for detection by autoradiography and avidin/biotin for antibody detection and affinity purification of antigens and antigen-bearing cells.

Also encompassed by the invention are hybridoma cell lines producing a monoclonal antibody wherein the antibody induces apoptosis in Her2 expressing cells and tissues. In one embodiment, the hybridoma produces a monoclonal antibody which recognizes an epitope on Her2 such that an antibody-Her2 complex results in induction of apoptosis. Preferably, the hybridoma produces an antibody which recognizes the epitope on Her2 which is recognized by mAb74. The hybridoma cell line which produces mAb74 has been deposited with the American Type Culture Collection, 10801 University Boulevard, Manassas, Va. 20110-2209, on Apr. 4, 1996, under accession no. HB 12078.

Various cancers are characterized by elevated levels of Her2 expression, including breast, ovarian, prostate, gastric and colorectal cancers (Press et al. in *Effects of Therapy on Biology and Kinetics of the Residual Tumor*, Part A: Preclinical Aspects pp. 209-221 (1990); Fukushige et al. Mol. Cell. Biol. 6, 955-958 (1986); Bargmann et al. in *The Oncogene Handbook* pp. 107-119 (1988)). A correlation between poor prognosis and Her2 overexpression in cancerous tissue has been reported. Patients with poor prognosis typically have a greater rate of relapse and a higher incidence of mortality. Often, such patients may benefit from an aggressive treatment regimen that includes high dose chemotherapy. Such therapy is expensive and may present risks to the patient. It has been proposed to use anti-Her2 antibodies in a cancer treatment regimen to inhibit tumor growth wherein the antibodies are used in conjunction with cytotoxic agents. One approach involves combinations of anti-Her2 antibodies and chemotherapeutic agents (such as cisplatin, 5-fluorouracil and others) to enhance the cytotoxic effect of chemotherapy drugs (this effect is referred to as antibody-dependent cellular cytotoxicity, or ADCC). A second approach uses immunotoxins or conjugates of antibodies with cytotoxic agents such as various A chain toxins, ribosomes inactivating proteins, and ribonucleases. Another approach involves the use of bispecific antibodies designed to induce cellular mechanisms for killing tumors (see, for example, U.S. Pat. Nos. 4,676,980 and 4,954,617).

The antibodies of the present invention are themselves toxic to Her2 expressing cells by inducing apoptosis. They may be used advantageously in the treatment of cancer characterized by Her2 overexpression, such as breast, ovarian, gastric, prostate and colorectal cancers. The use of the antibodies has significant advantages over previous approaches in that administration of cytotoxic agents which are deleterious to all growing cells can be avoided. It is anticipated that use of the antibodies alone to treat cancer will greatly reduce undesirable side effects associated with the administration of high dose cytotoxic agents or combinations of chemotherapy/antibody combination therapy. Alternatively, if a cytotoxic agent is used, use of the present antibodies in conjunction with cytotoxic agents is expected to be advantageous in that less cytotoxic agent may be used in order to achieve the same therapeutic effect. An antibody such as mAb74 may be administered alone or in combination with other anti-Her2 antibodies which induce apoptosis.

It is expected that the route of administration for the antibodies of the invention will be parenteral. Administration may be subcutaneous, intravenous or intramuscular injection and may be a single bolus injection or by continuous infusion. The amount of antibody to be used will vary depending upon the nature and severity of the condition but in general will range from about 0.1 µg/kg body weight to about 100 mg/kg body weight.

The invention provides for a pharmaceutical composition comprising a therapeutically effective amount of an anti-Her2 antibody which induces apoptosis with a pharmaceutically acceptable adjuvant. The adjuvant is selected from one or more of a diluent, carrier, preservative, emulsifier, anti-oxidant and/or stabilizer. Pharmaceutically acceptable adjuvants are known to one skilled in the art and are surveyed extensively in *Remington's Pharmaceutical Sciences* 18th ed. A. R. Gennaro, ed. Mack, Easton, Pa. (1990). The pharmaceutical compositions are sterile, non-pyrogenic and suitable for injection As used herein, a "therapeutically effective amount" refers to that amount of antibody which provides a therapeutic effect for a given condition and administration regimen. In the present invention, a therapeutic effect is induction of apoptosis in tumors characterized by Her2 overexpression. The antibodies are preferably those which will not elicit an immune response when administered to a patient in need of treatment. In one embodiment, the antibodies are human or humanized antibodies which may be prepared using procedures known to one skilled in the art.

The following examples are offered to more fully illustrate the invention, but are not construed as limiting the scope thereof.

EXAMPLE 1

Production of Her2, Her3 and Her4 Extracellular Domains

Cloning and Expression of Her2 Extracellular Domain (Soluble Her2)

A soluble Her2 receptor construct was made as follows. A cDNA clone of full-length Her2 in plasmid pLJ (pLJ is described in Korman et al. Proc. Natl. Acad. Sci. USA 84, 2150-2054 (1987) was digested with AatII which cuts once at position 2107 of the Her2 DNA sequence (numbering as in Coussens et al., supra). The linearized plasmid was cut with HindIII, which cuts 5' of the initiating ATG, to release an approximately 2200 bp fragment. This fragment was cloned into pDSRα2 5'-HindIII to 3'SalI using an oligonucleotide linker (AatII-SalI) which contained an in-frame FLAG sequence and a translation termination codon. The resulting cDNA encodes for the Her2 extracellular ligand binding domain spanning amino acid residues 1-653 fused to the FLAG sequence (underlined):

Thr Ser AspTyrLysAspAspAspAspAspLys STOP (SEQ ID NO: 1)

This construct was transfected into CHOd-cells. Single cell clones were derived from the selected population and assayed for soluble Her2 production by both anti-FLAG and anti-Her2 Western blot analysis.

Cloning and Expression of Her3 Extracellular Domain (Soluble Her3)

A cDNA clone containing the full-length Her3 sequence was isolated by screening a cDNA library prepared from the SKBR3 (American Type Tissue Collection, Bethesda, Md., ATCC HTB 30). The library was divided into 49 pools each containing 3200 individual clones. Plasmid DNA from each pool was transferred to nitrocellulose filter (Schleicher & Schuell, Keene, N.H.). Two oligonucleotide probes corresponding to the 3'-end of the Her-3 sequences

```
5'CCACCCGGGTTAGAGGAAGA 3' (SEQ ID NO: 2)
and

5'-AGTTACGTTCTCTGGGCATTA-3' (SEQ ID NO: 3)
``` were synthesized and used to screen the SKBR3 cDNA library filters. The hybridization was done in 6×SSC, 50 mM sodium-phosphate (pH 6.8), 0.1% sodium-pyrophosphate, 0.2% SDS, 2 mM EDTA, 2×Denhardt's solution and 50 mg/ml salmon sperm DNA at 42° C. for 16 hours. The filters were then washed at 42° C. with 2×SSC, 0.2% SDS, 2 mM EDTA for 30 minutes and exposed to X-ray films at −80° C. for 2 days.

Ten pools that gave positive signals in hybridization were further characterized by polymerase chain reaction (PCR) analysis to determine if they also encode the Her3 5' sequence. Plasmid DNA from each pool was amplified with oligonucleotide primers corresponding to the 5'-end of the Her-3 sequences:

```
5'CATGAGGGCGAACGACGCTCTG 3' (SEQ ID NO: 4)
and

5'CTTGGTCAATGTCTGGCAGTC 3' (SEQ ID NO: 5)
```

PCR was carried out for 40 cycles; with each cycle at 94° C., 30 seconds; 50° C., 30 seconds; and 72° C., 30 seconds. Three of the ten pools contained a full length Her3 cDNA. The three pools were rescreened by the colony hybridization procedure of Lin et al (Gene 44, 201-209. (1986)) until single clones were obtained from each pool. cDNA sequencing revealed a sequence identical to that published (Kraus et al., supra).

Plasmid pJT2-Her3 was used for PCR amplification of the soluble Her3 domain using the following primers:

```
                                                    (SEQ ID NO: 6)
Sense 5'CGCTCTAGACCACCATGAGGGCGAACGACGCTCTGCA 3'

(SEQ ID NO: 7)
Antisense 5'CGCGGATCCGTCGACTCACTATGTCAGATGGGTTT
TGCCGAT 3'
```

After digestion with the restriction enzymes XbaI and SalI, the 1.9 kb PCR fragment was subcloned into pDSRα2 (PCT Application No. WO91/05795) which had been cleaved with XbaI and SalI. The Her3 sequences in the resulting plasmid were confirmed by DNA sequencing. Plasmid pDSRα2/Her3 was used to transfect CHOd-cells for expression of soluble Her3.

Cloning and Expression of Her4 Extracellular Domain (Soluble Her4)

A full-length Her4 cDNA clone was obtained by screening a human fetal brain cDNA library (Stratagene, San Diego, Calif.). Two Her4 cDNA probes were prepared by PCR amplification of human brain cDNA (Clontech Laboratories, Inc., Palo Alto, Calif.). cDNA probe-1 corresponds to the Her4 5'-end sequences encoding amino acid residues 32 to 177 and cDNA probe-2 corresponds to the Her4 3'-end sequences encoding amino acid residues 1137 to 1254. (Plowman et al., supra) Approximately 4×10$^6$ pfu of the human fetal brain cDNA library were screened sequentially with the Her4 5'-end probe and the Her4 3'-end probe. The hybridization solution contained 6×SSC, 50 mM sodium-phosphate (pH 6.8), 0.2% SDS, 2 mM EDTA, 0.1% sodium-pyrophosphate, 2×Denhardt's solution, 50 mg/ml salmon sperm DNA and 50% formamide. Hybridization was at 42° C. for 16 hours. The filters were washed at 67° C. with 2×SSC, 0.2% SDS, 2 mM EDTA for 60 minutes and then exposed to x-ray films at −8° C. over night. Autoradiography of the filters showed that 12 clones hybridized to the 5'-end probe and another 5 clones hybridized to the 3'-end probe. Single clones were purified by re-plating, screened by probe hybridizations as described above and positive clones sequenced.

All positive cDNA clones which were sequenced were found to be partial Her4 cDNA clones. The sequences were found to be identical to the published Her4 sequence (Plowman et al. supra) except for a short deletion/replacement in the extracellular domain. Amino acids 626 to 648 of the published Her3 sequence (NGPTSHDCIYYPWTGHSTLPQHA (SEQ ID NO: 10)) were replaced by the peptide sequence IGSSIEDCIGLMD (SEQ ID NO: 11). Also, G at amino acid position 573 of Plowman's sequence was replaced by D.

As none of the 17 clones contained full length cDNA of Her4, two overlapping clones were fused together to generate a full length Her4 receptor using techniques described in Maniatis et al. (*Molecular Cloning: A Laboratory Manual* Cold Spring Harbor, N.Y.: Cold Spring Harbor Laboratory, (1982)). One clone encoded Her4 amino acid residues from 1 to 738 and another encoded amino acid residues from 588 to 1298. These two overlapping clones were released from plasmid pBluescriptSK-by restriction enzyme digestions and assembled in plasmid pGEM4 to generate a full length Her4 cDNA.

Soluble Her4 receptor was constructed by PCR amplification of a 700 bp Her4 DNA fragment encoding amino acids 409 to 639 from Her4 full length cDNA. The sequences of the two primers used in this amplification were

5' CCAAACATGACTGACTTCAGTG 3' (SEQ ID NO: 8)

and

5' GGCCAATTGCGGCCGCTTACTAATCCATCAGGCCGATGCAG TCTTC 3' (SEQ ID NO: 9)

PCR was carried out for 25 cycles; with each cycle at 94° C., 30 seconds; 55° C., 30 seconds; and 72° C., 30 seconds. This 700 bp PCR product was purified by agarose gel electrophoresis. Plasmid pGEM4/Her4 was digested with Not I and BstE II to produce two fragments: one containing plasmid pGEM4 and the Her4 5'-end cDNA encoding the extracellular domain of the receptor from amino acid 1 to 420; and a second fragment spanning amino acid 421 of Her4 to the end of the Her4 molecule These two DNA fragments were separated in agarose gel and the pGEM4/HER45'-end fragment was recovered. The 700 bp Her4 PCR fragment was digested with BstE II and Not I and was ligated with the pGEM4/HER45'-end fragment. The resulting cDNA encodes the Her4 receptor extracellular domain spanning amino acid residues from 1 to 639. The PCR amplified portion was sequenced to confirm that no PCR errors has occurred.

The soluble Her4 cDNA construct was released from plasmid pGEM4, inserted into plasmid pDSRa2 and transfected into CHOd⁻ cells using standard techniques (Maniatis et al., supra). Single cell clones were derived from the selected population and assayed for soluble Her4 production by BIAcore analysis.

Purification of sHer2, sHer3 and sHer4 Receptors.

Conditioned media of CHO cells expressing soluble Her2 (sHer2) was concentrated 12.5-fold with a Pellicon tangential flow ultrafiltration device (Amicon) fitted with a 50 K MWCO filter cassette (Filtron Technology), and the concentrate was diafiltered with three volumes of 20 mM potassium phosphate, 100 mM NaCl, pH 6.8. The diafiltered concentrate was mixed with hydroxylapatite (Calbiochem) equilibrated in diafiltration buffer. The unbound fraction was diluted with an equal volume of water and then applied to a Q-Sepharose fast flow column (Pharmacia) equilibrated in 10 mM potassium phosphate, 50 mM NaCl, pH 7.0. The column was eluted with a linear gradient from 50-600 mM NaCl. A pool was made from fractions containing >95% sHer2. sHer3 and sHer4 were also purified from conditioned media of CHO cells expressing these proteins in a similar fashion to the procedure described above. Due to its higher pI value, sHer3 was bound to and eluted from a Q-Sepharose column equilibrated in 10 mM potassium phosphate, 50 mM NaCl, pH 7.5.

EXAMPLE 2

Production of Anti-HER2 Antibodies

Procedures for immunizing animals, preparing fusions and screening hybridomas and purified antibodies were carried out generally as described in Harlow and Lane, *Antibodies: A Laboratory Manual*. Cold Spring Harbor Laboratory (1988).

Enzyme-Linked Immunosorbant Assay (EIA) 96-well plates were coated with 2 µg/ml sHer2, 2 µg/ml sHer3 or 2 µg/ml sHer4 in a carbonate-bicarbonate buffer. After blocking, hybridoma conditioned medium was added to the plate and incubated for 2 hours. The medium was aspirated and the plates were washed before addition of rabbit-anti-mouse IgG antibody conjugated with horseradish peroxidase (Boehringer Mannheim). After a one hour incubation, the plates were aspirated and washed five times. Bound antibody was detected with ABTS color reagent (Kirkegaard and Perry Labs., Inc.). The extent of antibody binding was determined by monitoring the increase in absorbance at 405 nm.

Cloning and IgG subtype determination. Single cell cloning was done in a 96-well plate using a limiting dilution method. Conditioned media of single cell clones were screened for antibody production using the EIA described above. The strongest antibody producing clones were chosen for cell growth expansion, subsequent subtype determination and competition studies.

BIAcore analysis. Purified sHer2, sHer3 or sHer4 were covalently coupled to a sensor chip CM5 via the primary amine group using 40 µl of the receptor in 10 mM Na acetate, pH 4.0 (10 µg receptor per ml). The unreacted groups on the sensor chip were blocked with an injection of 50 µl of 1 M ethanolamine hydrochloride (Pharmacia Biosensor AB). Each analysis cycle consisted of an injection of 40 µl of hybridoma supernatant (or purified mAbs), followed by injection of 10 µl of 10 mM HCl to regenerate the chip. Binding of the mAbs was detected by a change in SPR, measured in resonance units (RU). For most proteins, 1000 RU corresponds to a surface concentration of approximately 1 ng/mm².

Preparation and Screening of Hybridoma Cell Lines. 7 balb/C mice were injected subcutaneously three times at three week intervals with 10 µg of soluble Her2. The protein was emulsified with RIBI adjuvant. Serum titers to Her2 were evaluated at 8 weeks, and the two mice with the highest titers were selected and given a final IV injection of 10 µg of soluble Her2. Three days later, the two mice were euthanized, and spleens removed, disrupted in a Stomacher tissue disintegrator, and filtered, and single cells were recovered. After three washes, the spleen cells were counted, mixed with mouse myeloma cells (SP2/0) in a ratio of 3:1 (spleen: SP2/0) and fused in the presence of 50% PEG (MW 1500). The fused cells were plated in a total of 10 96-well plates at a spleen cell concentration of $1.25 \times 10^5$ per well in a medium consisting of DMEM:RPMI (1:1), 10% FBS and 10% ORIGEN. Selection of fused cells was carried out in HAT selection medium. Culture media were screened by EIA for antibodies to Her2 after viable cell colonies occupied approximately 30% of the well. Sixty eight positives were identified from 960 wells. Cells from 43 wells were cloned by limiting dilution to produce single-cell colonies. Wells containing single colonies were marked and, when grown to 30% of well area, were assayed for anti-Her2 antibodies by EIA and BIAcore. The final number of single cell clones was 26, representing 20 original masterwells.

Based on binding of hybridoma supernatants to sHer2 as assayed by EIA and BIACore, 10 clones were selected for further study. $5 \times 10^6$ cells from each of the 10 clones were injected into primed balb/C mice, and ascites fluid was collected at approximately 10 days. Immunoglobulins were affinity purified over a protein A MAPS II column (BioRad). The IgG purified antibodies were assayed by EIA for binding to Her2, Her3 and Her4 as described above. The binding capacity was evaluated at 10 ng/ml or 100 µg/ml of mAbs. Binding of antibodies to sHer2 was readily apparent at an antibody concentration of 10 ng/ml while binding to sHer3 and sHer4 was negligible even at an antibody concentration of 100 µg/ml. The data demonstrate that all clones except mab83 bind strongly to sHer2 with no detectable binding to sHer3 and sHer4.

IgG subtypes were determined on hybridoma supernatants using an Isotype Ab-Stat-Kit (Sangstate Medical Corp.) and the results are shown in Table I.

Binding of mAbs to sHer2, sHer3 and sHer4 Binding of mabs to sHer2 on a BIAcore chip was investigated using 10 μg/ml mAbs, and evaluated as resonance units (RU). As shown in Table I, two clones (52 and 58) showed greater than 1000 RU, 2 clones (35 and 42B) showed around 700 RU, 2 clones (43A and 74) showed around 300 RU, 2 clones (83 and 97) showed around 100 RU, and 2 clones (29 and 86) were less than 100 RU. The results indicated a wide range of affinity among the ten clones. No detectable binding of anti-sHer2 mAbs to sHer3 and sHer4 was observed. These results, along with the EIA data, confirm that the mAbs generated against sHer2 bind specifically to sHER2 with little or no binding to sHer3 and sHer4.

$H_2O$ before adding 3 units of recombinant N-glycanase (Genzyme). The reaction was allowed to proceed with gentle shaking at 37° C. for 20 hrs.

An ECL glycoprotein detection system kit (Amersham Life Science) was used to determine the extent of deglycosylation. 0.25 μg each of sHer2 and deglycosylated sHer2 were run on a 4-20% gel (Novex) under nonreducing conditions and then blotted to nitrocellulose (Schleicher & Schuell) for 1 hour at 90 volts in a Bio-Rad mini PROTEAN II apparatus (BioRad) with cooling. After blotting, the membrane was treated with 10 mM sodium metaperiodate for 20 minutes, then 300 nM biotin hydrazide for 60 minutes, both in 100 mM sodium acetate, pH 5.5 at room temperature. After each step, the membrane was washed with three changes of PBS. Nonfat dry milk (Carnation) was added to PBS at a concentration of 5% (w/v) and incubated overnight at 4° C. to block nonspe-

TABLE I

Immunological properties of anti-Her2 mAbs

| MONO-CLONAL ANTIBODY ID | IGG SUB-TYPE | EPITOPE GROUPING BY BIA-CORE | BINDING TO sHER2 BIA CORE RU OF 10 UG/ML | BINDING TO sHER3 BIA CORE RU OF 10 UG/ML | BINDING TO sHER4 BIA CORE RU OF 10 UG/ML | BINDING TO sHER2 EIA PLATE O.D. OF 10 NG/ML | BINDING TO sHER3 EIA PLATE O.D. OF 100 UG/ML | BINDING TO sHER4 EIA PLATE O.D. OF 100 UG/ML |
|---|---|---|---|---|---|---|---|---|
| 35 | 1 | G1 | 781 | −5 | −15 | 0.97 | 0.1 | 0.11 |
| 42B | 1 | G2 | 745 | −23 | −15 | 2.35 | 0.1 | 0.09 |
| 43A | 2A | G2 | 392 | −5 | −18 | 2.25 | 0.24 | 0.19 |
| 52 | 2B | G2 | 1600 | −7 | −18 | 2.45 | 0.25 | 0.23 |
| 58 | 1 | G2 | 1266 | 2 | −17 | 2.63 | 0.09 | 0.1 |
| 74 | 1 | G3 | 372 | 15 | −13 | 1.19 | 0.22 | 0.19 |
| 29 | 1 | G4 | 76 | 0 | −20 | 2.28 | 0.52 | 0.35 |
| 83 | 1 | G4 | 115 | −4 | −16 | 0.09 | 0.37 | 0.21 |
| 86 | 1 | G4 | 62 | −9 | −20 | 2.31 | 0.63 | 0.35 |
| 97 | 1 | G4 | 109 | −4 | −17 | 2.36 | 0.26 | 0.16 |
| Mouse IgG | | | | | | 0.09 | 1.2 | 0.9 |

Epitope Competition assay. The epitope specificity of anti-sHer2 mAbs was determined by binding pairs of monoclonal antibodies simultaneously to sHer2 immobilized on a BIA-core chip. mAbs directed against different epitopes should bind independently of each other, whereas mabs directed against closely related epitopes should interfere sterically with each other's binding. The first mAb was injected three times in a volume of 40 μl at a concentration of 10 μg/ml onto the immobilized sHer2 surface. A 40 μl of the second mAb was then injected and the ability to simultaneously bind to the sHer2 was evaluated. The biosensor surface was regenerated by the injection of 10 μl of 50 mM HCl. Binding was also analyzed when the injection sequence of each pair of mAbs was reversed. This analysis divided the mAbs into 4 different groups of epitope specificity, as shown in Table I. No correlation between epitope grouping and phosphorylation activity was apparent except for mAb74, which appears to have a unique epitope from the other mAbs.

EXAMPLE 3

Characterization of mAb74 Epitope on Her2

The effect of glycosylation on mAb74 interaction with sHer2 was determined as follows. Sixty μg of sHer2 in 20 mM BTP, 40 mM NaCl, pH 7.4, was denatured for five minutes in a boiling water bath in the presence of 0.4% SDS. After denaturation, NP-40 (Boehringer Mannheim) was added to 2% v/v, and the reaction diluted with an equal volume of DI cific binding. The membrane was incubated at room temperature with streptavidin horseradish peroxidase conjugated with ECL detection reagents for one minute. The blot was exposed to Hyperfilm-ECL (Amersham Life Science). No protein band was observed in the deglycosylated sample (FIG. 1A) indicating complete deglycosylation had occurred.

Intact and deglycosylated sHer2 (25 ng each) were loaded and run on a 4-20% gel (Novex) under reducing and nonreducing conditions. The Gel was blotted 1 hr at 90 volts, blocked with 5% nonfat dry milk and detected with 0.4 μg/ml mAb74 followed by ⅕₀₀₀ anti-mouse conjugated horseradish peroxidase after three 10 min washes in PBS 0.1%, Tween 20. An ECL kit (Amersham Life Science) was used for detection. mAb74 was observed to bind to both glycosylated and deglycoslated sHer2 under nonreducing conditions (FIG. 1B). No antibody binding was observed under reducing conditions.

EXAMPLE 4

Dimerization of Her2 by Anti-Her2 Antibodies

Typically, antibodies have two binding sites for antigens, so it may be expected that antibodies which bind receptors can promote receptor dimerization. Size exclusion chromatography (SEC) with light scattering detection was used to determine the stoichiometry of anti-Her2 antibody binding to sHer2. The use of SEC with on-line light scattering has advantages over SEC alone for determining the molecular weight or stoichiometry of a protein complex. While the elution position of a protein or complex is indicative of molecular weight using conventional SEC, a light scattering measurement is independent of the elution position of a protein or a complex. In addition, the molecular weight from light scattering reflects only the polypeptide if the extinction coefficient of the polypeptide alone is used in the analysis. The on-line light scattering/size exclusion chromatography system uses three detectors in series: a light scattering detector (Wyatt Minidawn), a refractive index detector (Polymer Laboratories PL-RI), and a UV absorbance monitor at 280 nm (Knauer A293). A Superdex 200 (Pharmacia) SEC column equilibrated with Dulbecco's phosphate-buffered saline (PBS) and a 100 µl sample loop were used. The system was operated at a flow rate of 0.5 ml/min. The complexes of anti-sHer2 mAb and sHer2 were made by mixing 55 µl of 1.5 mg/ml mAb35, 0.8 mg/ml mAb52, 1.2 mg/ml mAb58, 1.6 mg/ml mAb42, 0.84 mg/ml mAb74, and 0.89 mg/ml mAb83 with 55 µl of 2.0, 2.0, 1.3, 2.0, 2.0, and 2.0 mg/ml sHer2, respectively. The complexes of the above mAbs and sHer3 were made in a similar way. 100 µl samples of each complex were injected onto a Superdex 200 column and the elution was monitored by light scattering, refractive index and UV absorbance detectors.

For a glycoprotein complex, the molecular weight of its polypeptide is proportional to $(uv)(LS)/[e_p(RI)^2]$ (Takagi J. Chromatogr. 506, 409-446 (1990); Arakawa et al. Arch. Biochem. Biophys. 308, 267-273 (1994); Philo et al. J. Biol. Chem. 269, 27840-27846 (1994) where uv, LS, and RI are the signals from the absorbance, light scattering, and refractive index detectors, respectively, and $e_p$ is the extinction coefficient (the absorbance of a 1 mg/ml solution for 1 cm pathlength) of the polypeptide. For a complex with a known stoichiometry ($A_m B_n$), its extinction coefficient can be calculated with the equation $\epsilon_p = (m \times \epsilon_A \times M_A + n \times \epsilon_B \times M_B)/(m \times M_A + n \times M_B)$ where $\epsilon_A$, $\epsilon_B$, $M_A$ and $M_B$ are the polypeptide extinction coefficient and molecular weight of either protein A or B.

In order to obtain the molecular weight and stoichiometry of a glycoprotein complex, one must calculate its extinction coefficient. However, the extinction coefficient of a complex cannot be calculated unless stoichiometry is known. A self-consistent method is used to solve this problem, assuming various possibilities for the stoichiometry of the complex. For each assumed stoichiometry, an extinction coefficient and corresponding experimental molecular weight is calculated. Finally, the stoichiometry with the best consistency between the experimental and theoretical molecular weight is selected as the correct stoichiometry for the complex. The results of this method are shown in Table II.

TABLE II

Binding of mAb to sHer2 determined by SEC/light scattering

| Proteins or Complexes | $\epsilon$ L g·cm | Experimental MW × 10⁻³ | Theoretical MW × 10⁻³ | Correct Assumption? |
|---|---|---|---|---|
| sHer2 | 0.85 | 69 | | |
| mAb35 | 1.4 | 139 | | |
| mAb52 | 1.4 | 151 | | |
| mAb58 | 1.4 | 142 | | |
| mAb42b | 1.4 | 136 | | |
| mAb74 | 1.4 | 145 | | |
| mAb83 | 1.4 | 141 | | |
| Assumption of sHer2-mAb35 Complex Stoichiometry: | | | | |
| 1sHer2:1mAb35 | 1.24 | 237 | 208 | No |
| 2:1 | 1.14 | 261 | 277 | Yes |
| 3:1 | 1.08 | 275 | 346 | No |
| 1:2 | 1.31 | 226 | 347 | No |
| 1:3 | 1.41 | 208 | 486 | No |
| Assumption of sHer2-mAb52 Complex Stoichiometry: | | | | |
| 1sHer2:1mAb52 | 1.24 | 252 | 220 | No |
| 2:1 | 1.14 | 275 | 289 | Yes |
| 3:1 | 1.08 | 289 | 358 | No |
| 1:2 | 1.31 | 240 | 371 | No |
| 1:3 | 1.41 | 223 | 522 | No |
| Assumption of sHer2-mAb58 Complex Stoichiometry | | | | |
| 1sHer2:1mAb58 | 1.24 | 252 | 211 | No |
| 2:1 | 1.14 | 272 | 280 | Yes |
| 3:1 | 1.08 | 289 | 348 | No |
| 1:2 | 1.31 | 237 | 353 | No |
| 1:3 | 1.41 | 220 | 522 | No |
| Assumption of sHer2-mAb42b Complex Stoichiometry | | | | |
| 1sHer2:1mAb42b | 1.24 | 246 | 205 | No |
| 2:1 | 1.14 | 266 | 274 | Yes |
| 3:1 | 1.08 | 281 | 343 | No |
| 1:2 | 1.31 | 232 | 341 | No |
| 1:3 | 1.41 | 214 | 477 | NO |
| Assumption of sHer2-mAb74 Complex Stoichiometry | | | | |
| 1sHer2:1mAb74 | 1.24 | 258 | 214 | No |
| 2:1 | 1.14 | 281 | 283 | Yes |
| 3:1 | 1.08 | 298 | 352 | No |
| 1:2 | 1.31 | 245 | 359 | No |
| 1:3 | 1.41 | 228 | 504 | No |

*The molecular weights (MW) in the table reflect polypeptide only.

The experimental molecular weights (excluding carbohydrate) for the complexes are most consistent with the theoretical values assuming 2 sHer2 per 1 mAb for each of the 5 mAbs tested. This proves that these antibodies could dimerize Her2 expressed on the cell surface. However, since the sHer2 and mAbs were mixed at 2:1, the observed results do not exclude the possibility of 1 sHer2:1 mAb complex formation when the mAb is present in excess. No complex was observed for sHer2 and mAb83 mixture. This may be caused by weak binding and complex dissociation during the chromatographic procedure. The samples containing sHer2 mAb at a 2:1 molar ratio eluted as a single peak, suggesting formation of 2 sHer2:1 mAb complex without dissociation during elution.

In order to verify that these antibodies do not dimerize Her3, similar experiments were done using mixtures of mAbs and sHer3. No complexes between sHer3 and any of the mabs were detected.

EXAMPLE 5

Receptor Phosphorylation by Anti-Her2 Antibodies

Adherent cells (SKBR3 or MDAMB453) were grown in 48 well plates and washed with DMEM 2-3 times. Suspension cells (32D, Her2/32D, HEG/32D) were pelleted by centrifugation and washed with PBS. HEG/32D is a cell line transfected with a chimeric Her2/EGF receptor (HEG) having an extracellular domain from Her2 spanning amino acid residues 1-653 and intracellular and transmembrane domains from EGF receptor spanning amino acid residues 646-1210. mAb solution or control ligand solution was added to the well or to the pelleted tube and incubated for 5 min at 37° C. The solution was removed and the cells were solubilized with SDS sample buffer. The samples were subjected to SDS-PAGE followed by Western blotting and probing with anti-phosphotyrosine.

Figure 2A:
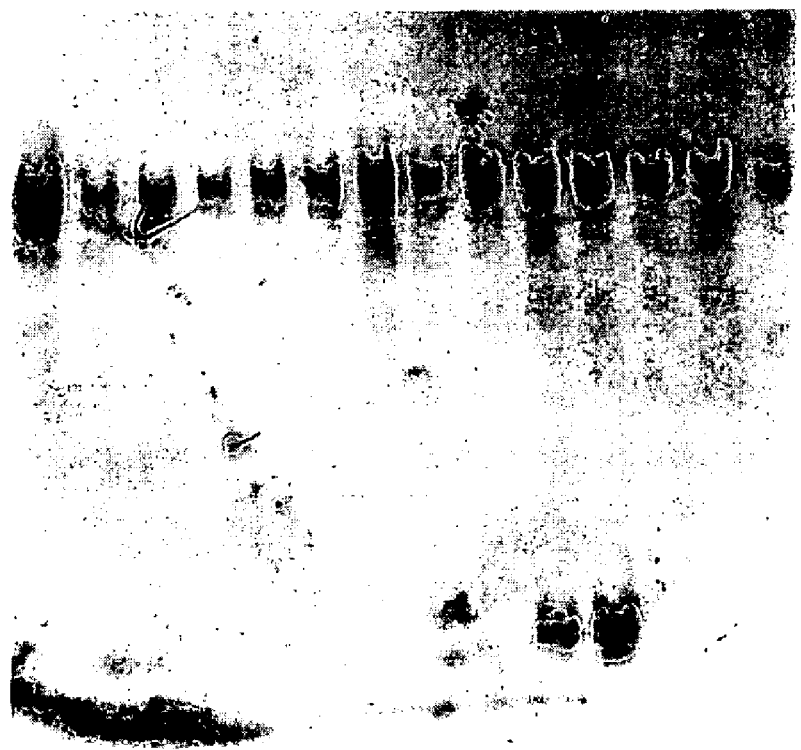
FIG. 2. Her2 and Her3 tyrosine phosphorylation induced by mAb stimulation in SKBR3. SKBR3 cells were seeded in a 48-well plate for 5 min at 37° C. for 18 hours before mAb stimulation. Cells were solubilized with SDS sample buffer. Solubilized samples were electrophoresed on 6% polyacrylamide gels, followed by Western blotting and probing with anti-phosphotyrosine antibody. (a) All mAb concentrations were 250 nM in DMEM. 2 nM neu differentiation factor-α (NDFα) was used as a positive control. (b) mAb dose dependence of tyrosine phosphorylation.
Figure 2B:
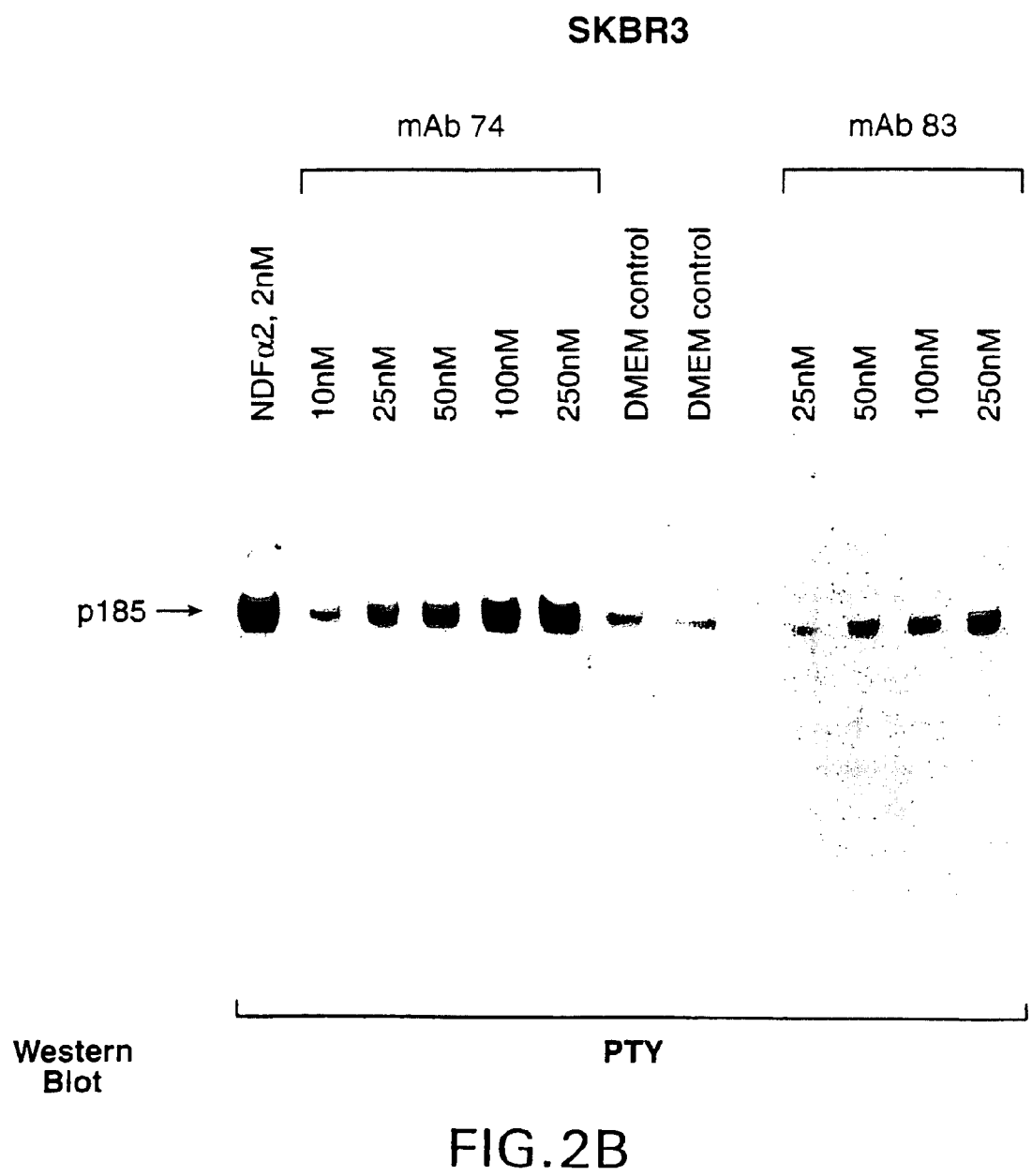

Twelve clones of anti-sHer2 mAbs were tested for stimulation of receptor tyrosine phosphorylation in SKBR3 cells. As shown in FIG. 2-a, mAb74, 52, and 83 strongly stimulated the tyrosine phosphorylation of 180-185 kDa proteins in SKBR3 cells in which both Her2 and Her3 were identified. The phosphorylation was dose dependent (FIG. 2-b). As shown in FIG. 3, the phosphorylation of SKBR3 cells by mAb 74, 52 and 83 was inhibited with sHer2. To determine which receptor is phosphorylated, Her2 and Her3 were immunoprecipitated from SKBR3, and Her2, Her3 and Her4 were immunoprecipitated from MDAMB453 after mAb incubation and analyzed by Western blots probed with anti-phosphotyrosine. Her2 and Her3 in SKBR3 or Her2, Her3 and Her4 in MDAMB453 were all tyrosine phosphorylated.

Figure 4:
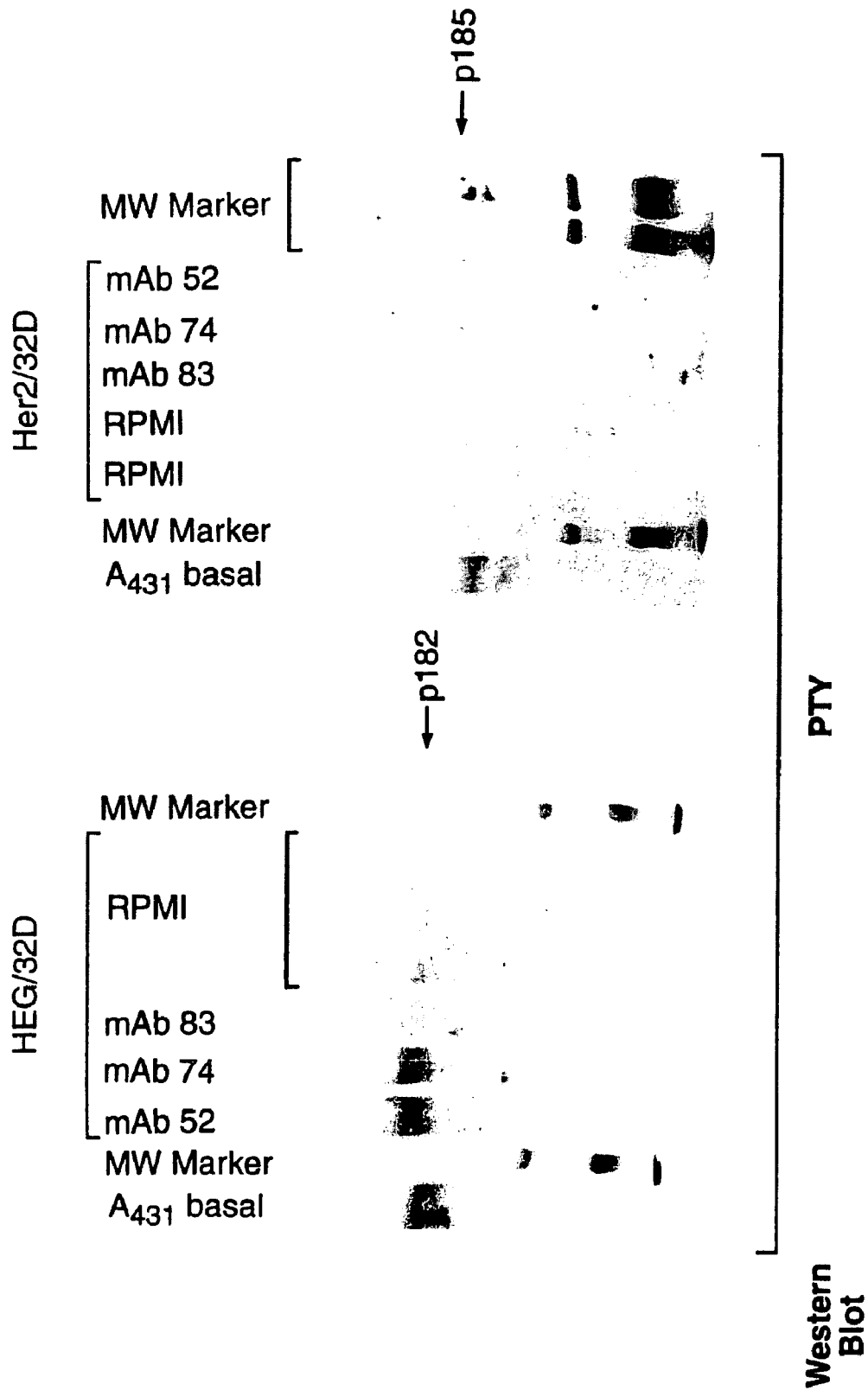
FIG. 4. Receptor tyrosine phosphorylation of transfected cell lines, Her2/32D and HEG/32D, induced by mAb stimulation. For phosphorylation assay, cells were pelleted by centrifugation, washed with PBS, and then incubated with 100 µl of 250 nM mAbs in RPMI for 5 min at 37° C., followed by quenching with the addition of 1 ml ice cold PBS and centrifugation at 4° C. Supernatant was removed and SDS sample buffer added to the centrifuged pellet. The sample was subjected to 6% SDS-PAGE followed by Western blotting and probing with anti-PTY. A431 basal phosphorylated sample was used as a positive control.

A similar assay has been done with transfected cell lines, Her2/CHO and Her2/32D, to study the direct interaction of mAb and Her2. mAbs 52, 74 and 83 failed to stimulate phosphorylation of Her2 in Her2/CHO and Her2/32D transfected cells (FIG. 4 shows data for Her2/32D cells only). By contrast, the Her2/EGF chimeric receptor was phosphorylated in HEG/32D (FIG. 4). A subsequent experiment was performed using a Her2/32D transfectant which expressed Her2 at levels comparable to those of the HEG chimeric receptor shown in FIG. 4. Under these conditions, mAb74 stimulates Her2 phosphorylation in Her2/32D cells. The results suggest that mAb74 activates Her2 kinase by homodimerization in Her2/32D cells but may activate by heterodimerization in SKBR3 cells.

EXAMPLE 6

Cell Morphologic Change and Apoptosis Induced by Anti-Her2 Antibodies

Cell morphologic change. Cells were seeded in 5 cm dishes to about 20% confluency and mAbs added after 18 hr. After 5 days, cells were observed with light microscopy, photographed, and counted.

Figure 5A:
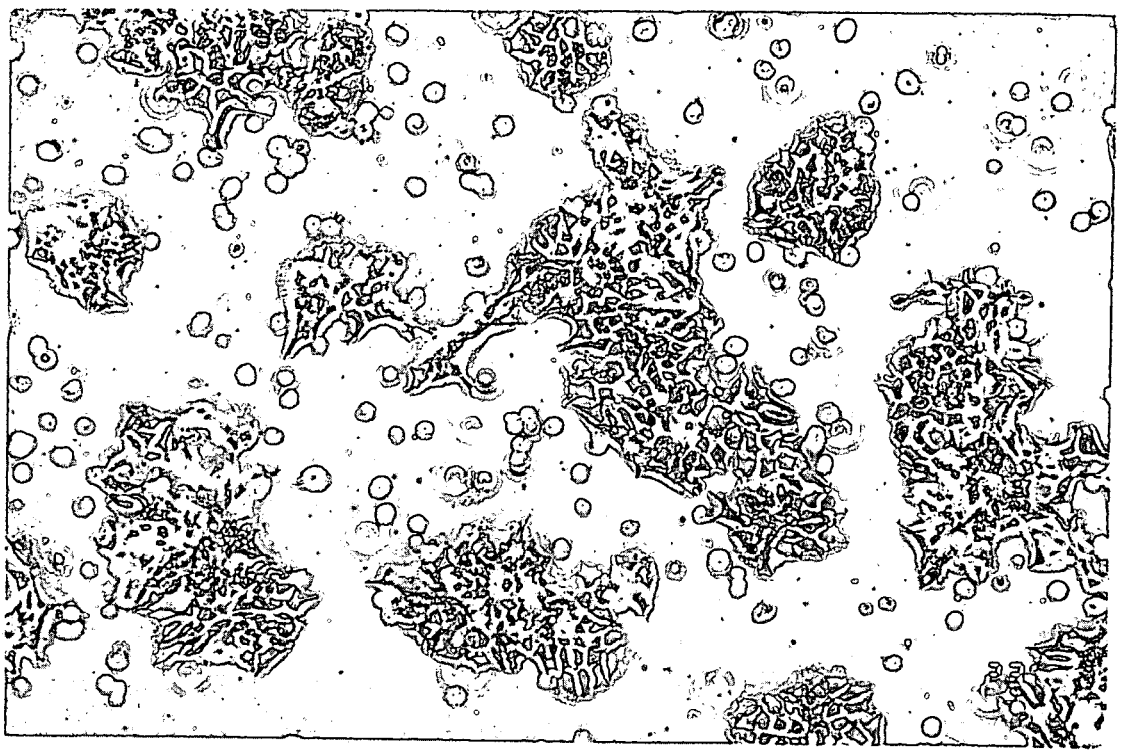
FIG. 5. Cell morphologic change induced by mAbs. Cells (a-d, Her2/MCF7; e, f, MDAMB453) were grown in 1% FBS in culture media with or without mAb. After 5 days, cells were observed and photographed. (a, e) control (without mAb). (b) 250 nM mAb74. (c) 250 nM mAb83. (d) 250 nM mAb42b. (f) 100 nM mAb74.
Figure 5B:
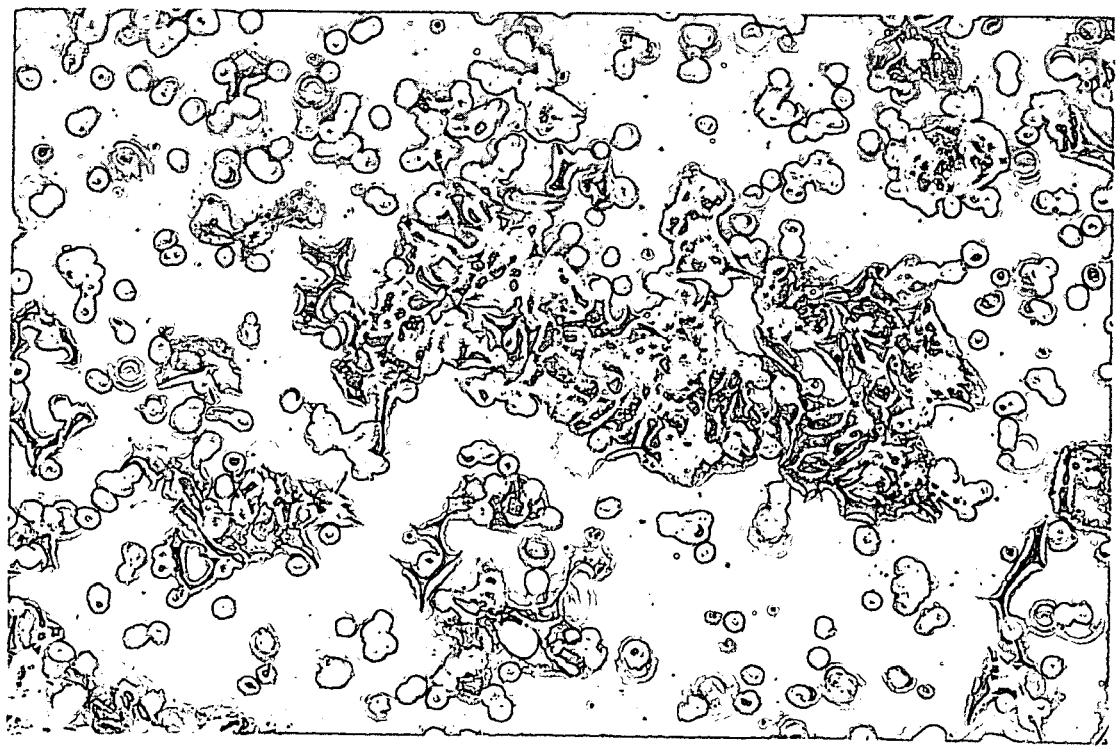
Figure 5C:
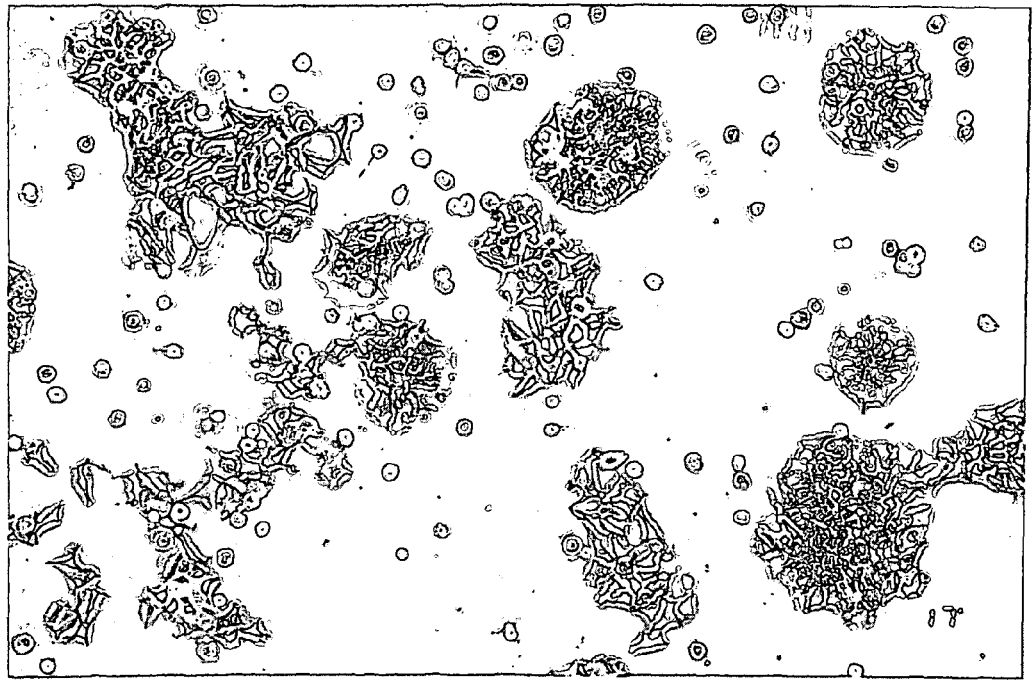
Figure 5D:
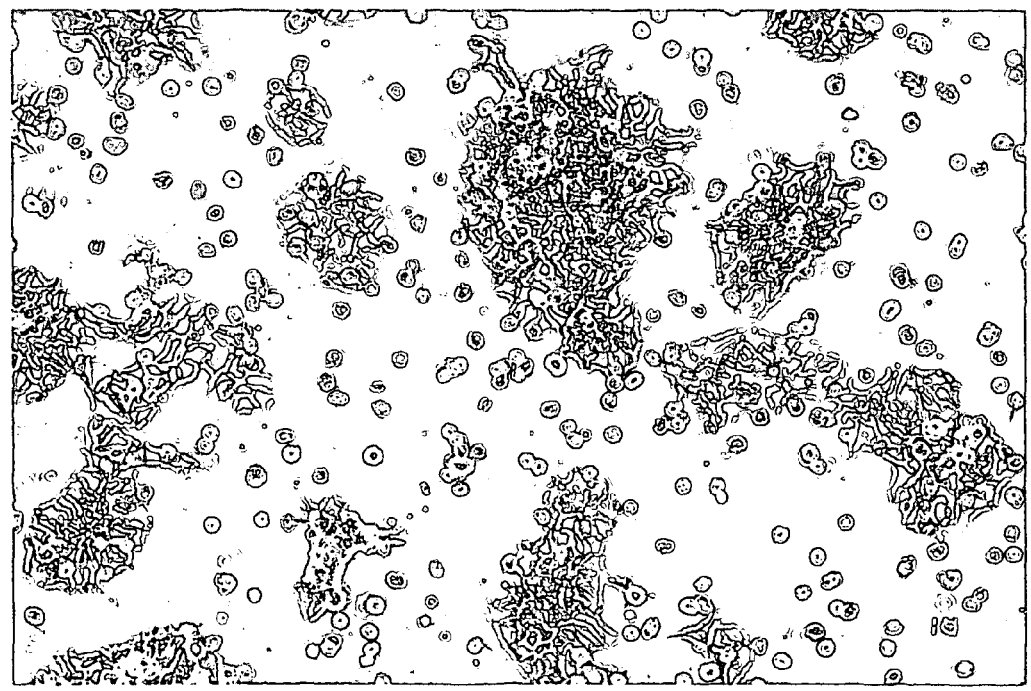
Figure 5E:
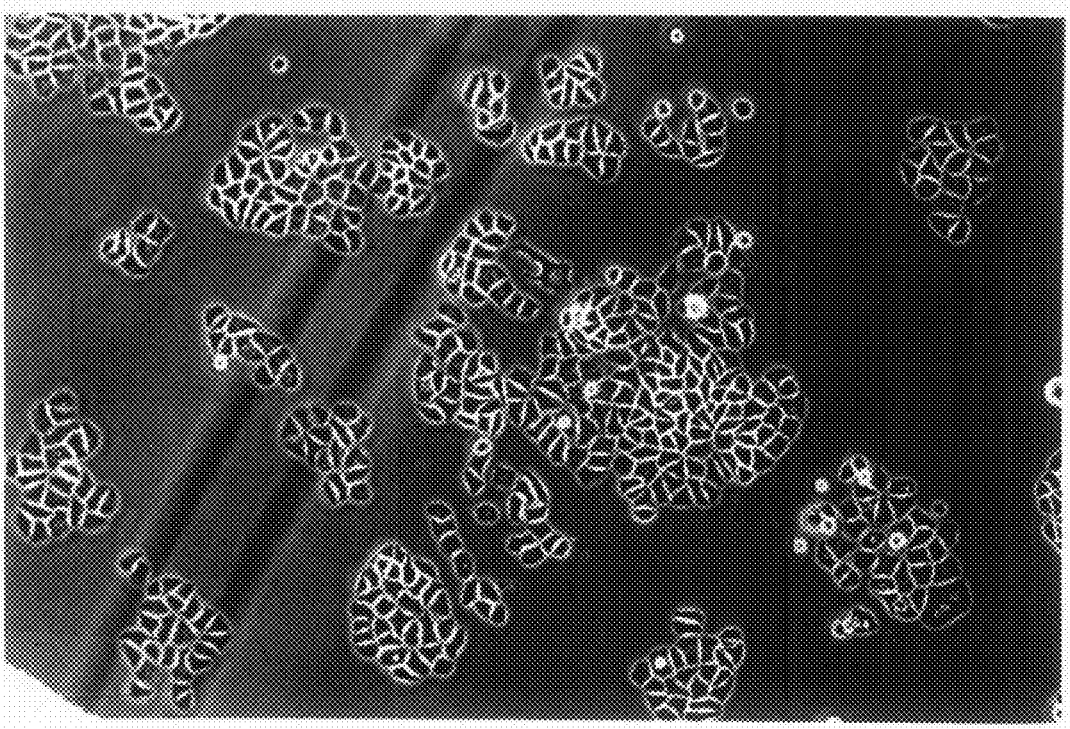
Figure 5F:
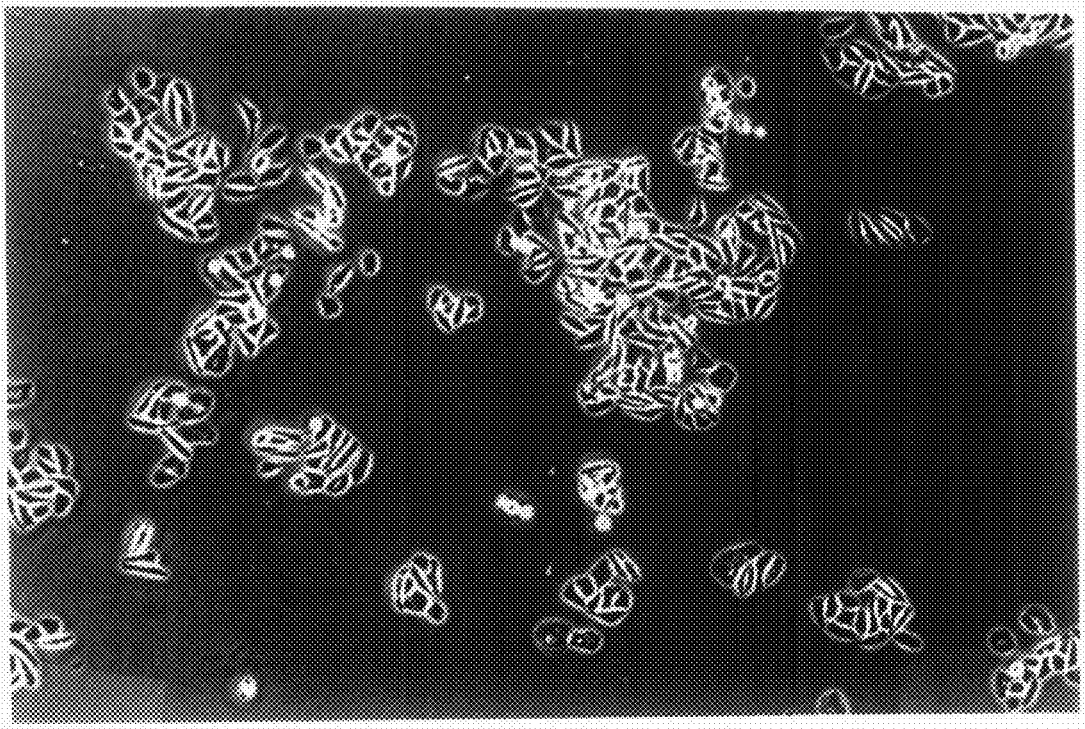
Figure 6A:
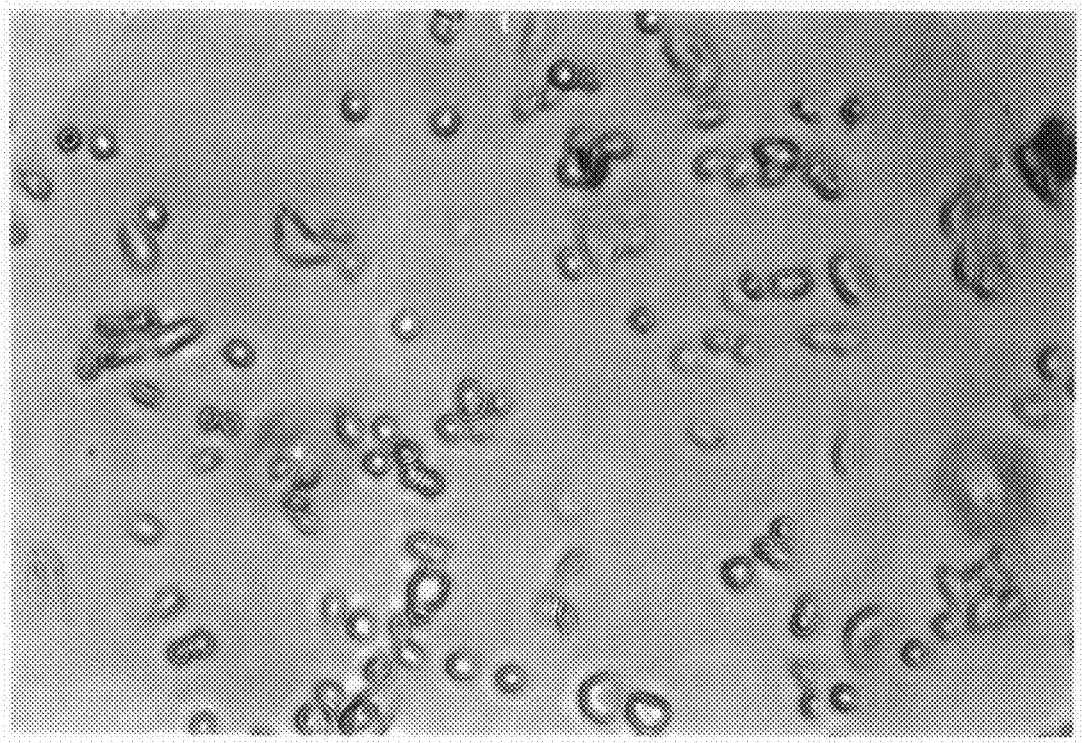
FIG. 6. Detection of apoptotic cells with a modified TUNEL method. MDAMB453 (a-d) cells or Her2/MCF7 (e, f) cells were incubated with or without mAbs in 1% FBS culture media for one day followed by an apoptosis assay. (a, e) control (without mAb). (b) 50 nM mAb74. (c, f) 500 nM mAb74. (d) 500 nM mAb42b.
Figure 6B:
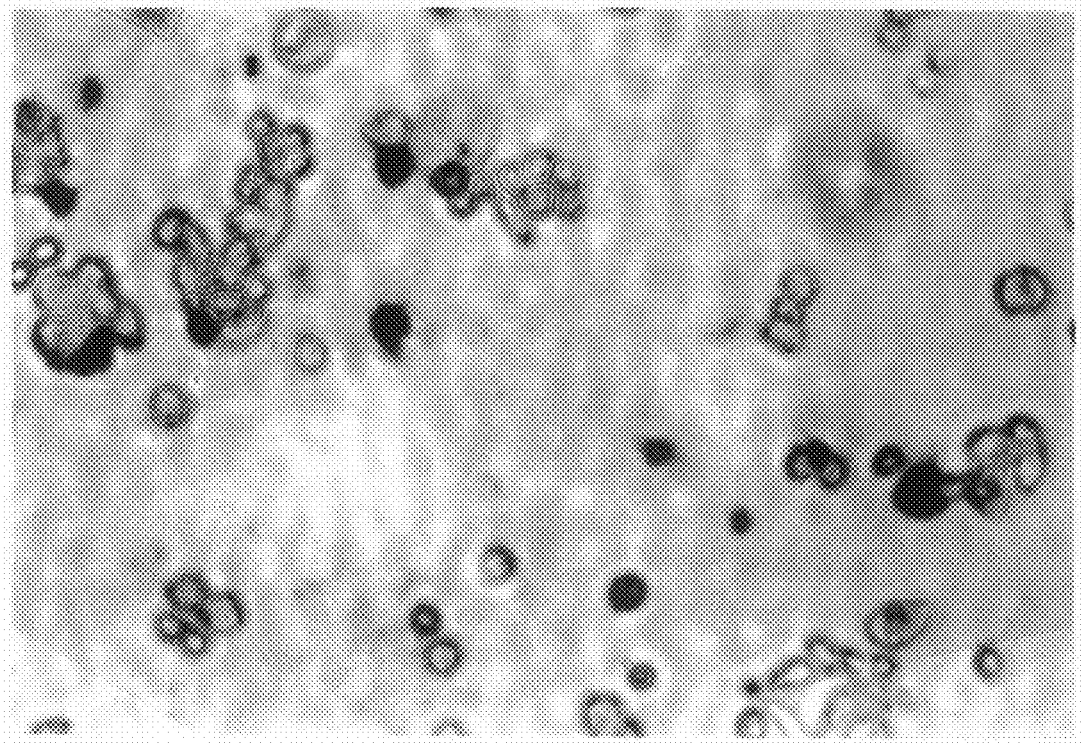
Figure 6C:
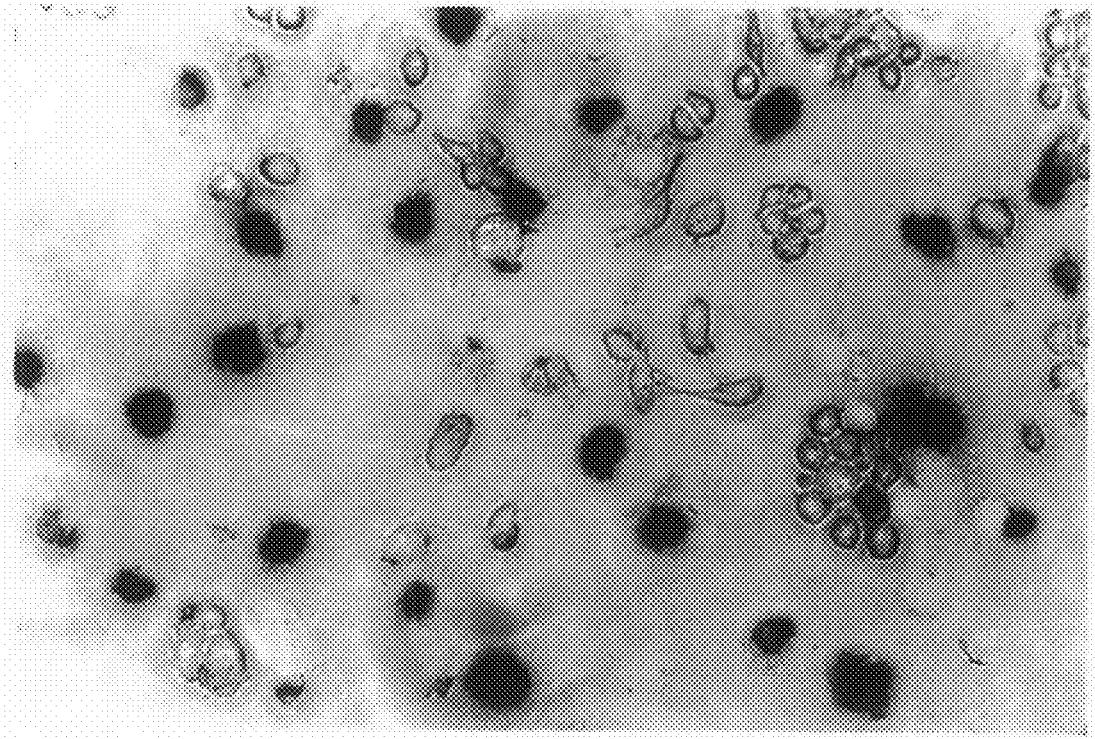
Figure 6D:
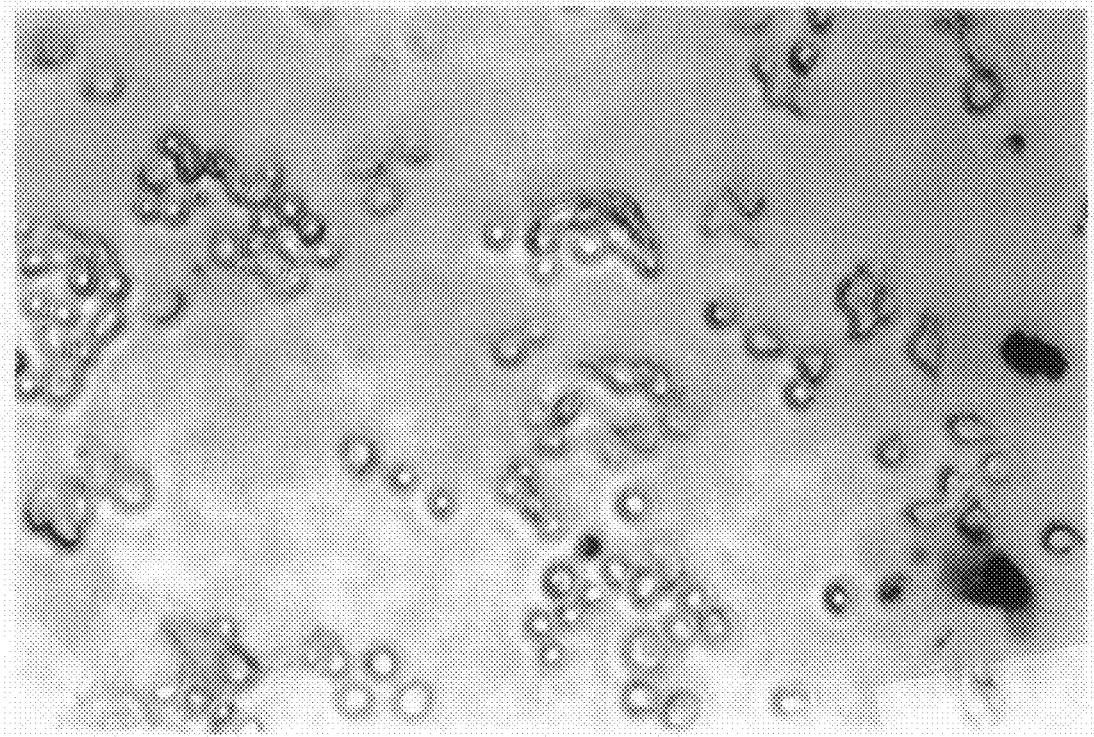
Figure 6E:
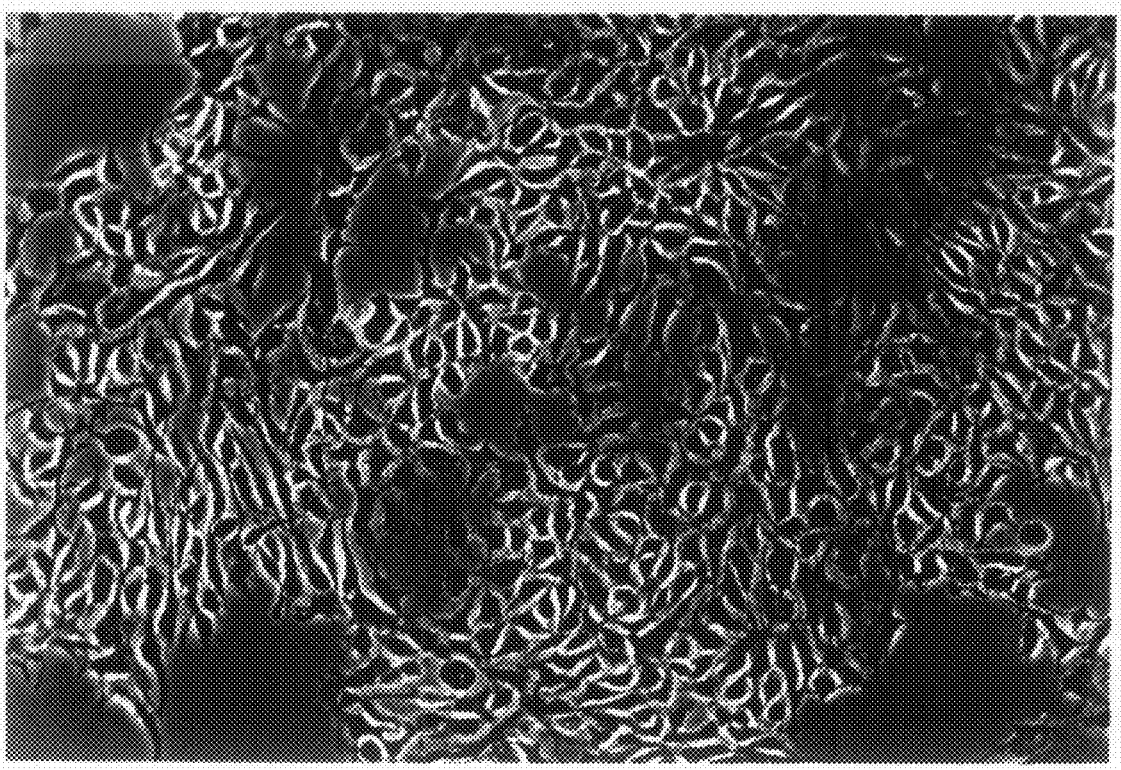
Figure 6F:
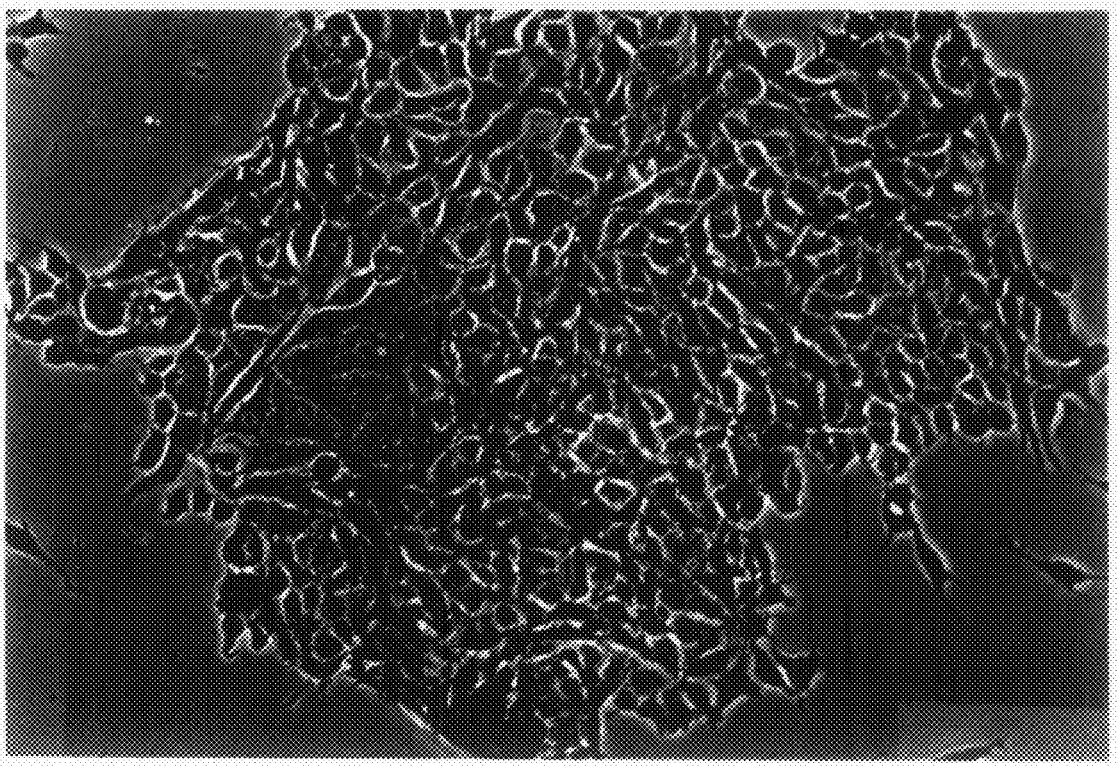

Her2/MCF7 cells were incubated with 250 nM mAb42b, mAb83 and mAb74. After 5 days incubation, mAb74 caused extensive cell death and a dramatic cell morphology change, primarily elongation of the cell, as shown in FIG. 5. mAb83 caused a moderate cell morphology change and 42b resulted in little change. The viable cell number after mAb74 incubation with Her2/MCF7 cells for five days was only 36% of the control done without mAb incubation. mAb74 also induced cell morphological changes in MDAMB43 cells (FIG. 5F).

Cell apoptosis. Cells were seeded in 8-well Chamber Slide (Nunc) to about 60-70% confluency and after 18 hr, culture media was changed to 1% FBS-containing media with or without mAb. On day one, cells were fixed with 4% neutral-buffered formalin (NBF) followed by three washes with PBS. After cells were dried, apoptosis was detected using a modified TUNEL method. TUNEL detects 3'-OH DNA ends generated by DNA fragmentation by labeling the ends with digoxigenin-conjugated dUTP using terminal deoxynucleotidyl transferal and then incubating with horseradish peroxidase (HRP)-conjugated anti-digoxigenin. Bound HRP was detected with the substrate, 3-amino-9-ethylcarbazole (Sigma). Most of the reagents were used from Apop Tag in situ apoptosis detection kit (Oncor). HRP-conjugated antibodies were from Boehringer Mannheim.

We found that mAb74 has the strongest effect on receptor tyrosine phosphorylation (FIG. 1A), cell morphology change (FIG. 5) and cell death. To clarify the mechanism of the cell death caused by mAb74, we examined apoptosis by a modified TUNEL method. As shown in FIG. 6, cells incubated with mAb74 for one day showed apoptosis as detected by red color using the TUNEL method, while incubation with mAb42b was barely apoptotic in MDAMB453 and Her2/MCF7 (MCF7 cells transfected with full-length Her2). The number of apoptotic cells induced by 50 nM mAb74 was about 10% of the number induced by 500 nM mAb74, indicating that apoptosis by mAb74 is dose dependent (FIG. 6). mAb74 also induced apoptosis in Her2/MCF7 cells. After 5 days of incubation with mAb74, live cells were still present in culture but no apoptosis could be detected suggesting that apoptotic cells were detached and live cells were not undergoing an apoptotic process. The surviving cells had undergone morphological changes such as those seen in FIG. 5.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

The invention claimed is:

1. A method for treating cancer characterized by overexpression of Her2, in a patient, comprising administering to the patient an antibody or fragment thereof that binds an eptiope on Her2 which is recognized by a monoclonal antibody produced by hybridoma cell line ATCC No. HB 12078, wherein the antibody or fragment thereof is conjugated to a cytotoxic agent.

2. The method of claim 1, wherein the cytotoxic agent is selected from an A chain toxin, a ribosome inactivating protein, and a ribonuclease.

3. The method of claim 1, wherein the antibody or fragment thereof is a monoclonal antibody.

4. The method of claim 1, wherein the antibody or fragment thereof is a humanized antibody.

5. The method of claim 1, wherein the antibody or fragment thereof is a human antibody.

6. The method of claim 1, wherein the antibody or fragment thereof is a F(ab) or Fab' fragment.

7. The method of claim 1, wherein the antibody or fragment thereof is produced by the hybridoma cell line ATCC No. HB 12078.

8. The method of claim 1, wherein the cancer is selected from breast cancer, ovarian cancer, prostate cancer, gastric cancer, and colorectal cancer.

9. The method of claim 1, wherein the overexpression of Her2 is at least 10% higher than a normal basal level.

10. The method of claim 1, wherein the overexpression of Her2 is at least 20% higher than a normal basal level.

11. The method of claim 1, wherein the overexpression of Her2 is at least 30% higher than a normal basal level.

12. The method of claim 1, wherein the antibody or fragment thereof is administered parenterally, subcutaneously, intravenously, or intramuscularly.

* * * * *

SEQUENCE LISTING

```
<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: FLAG tag

<400> SEQUENCE: 1

Thr Ser Asp Tyr Lys Asp Asp Asp Asp Lys
 1               5                  10

<210> SEQ ID NO 2
<211> LENGTH: 20
<212> TYPE: DNA
<213> ORGANISM: Artificial Sequence
```

```
<220> FEATURE:
<223> OTHER INFORMATION: Description of Artificial Sequence:
      oligonucleotide probe

<400> SEQUENCE: 2
ccacccgggt tagaggaaga                                              20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 3
agttacgttc tctgggcatt a                                            21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 4
catgagggcg aacgacgctc tg                                           22

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 5
cttggtcaat gtctggcagt c                                            21

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: PCR primer

<400> SEQUENCE: 6
cgctctagac caccatgagg gcgaacgacg ctctgca                           37

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: PCR primer

<400> SEQUENCE: 7
cgcggatccg tcgactcact atgtcagatg ggttttgccg at                     42

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 8
```

```
ccaaacatga ctgacttcag tg                                              22

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: PCR primer

<400> SEQUENCE: 9
ggccaattgc ggccgcttac taatccatca ggccgatgca gtcttc                    46

<210> SEQ ID NO 10
<211> LENGTH: 23
<212> TYPE: PRT
<213> ORGANISM: Homo sapiens

<400> SEQUENCE: 10

Asn Gly Pro Thr Ser His Asp Cys Ile Tyr Tyr Pro Trp Thr Gly His
 1               5                  10                  15

Ser Thr Leu Pro Gln His Ala
            20

<210> SEQ ID NO 11
<211> LENGTH: 13
<212> TYPE: PRT
<213> ORGANISM: Homo sapiens

<400> SEQUENCE: 11

Ile Gly Ser Ser Ile Glu Asp Cys Ile Gly Leu Met Asp
 1               5                  10
```